(12) United States Patent
Ivanov et al.

(10) Patent No.: US 8,691,088 B2
(45) Date of Patent: Apr. 8, 2014

(54) NARROW I.D. MONOLITHIC CAPILLARY COLUMNS FOR HIGH EFFICIENCY SEPARATION AND HIGH SENSITIVITY ANALYSIS OF BIOMOLECULES

(75) Inventors: Alexander R. Ivanov, East Boston, MA (US); Li Zang, Malden, MA (US); Barry L. Karger, Newton, MA (US)

(73) Assignee: Northeastern University, Boston, MA (US)

( * ) Notice: Subject to any disclaimer, the term of this patent is extended or adjusted under 35 U.S.C. 154(b) by 2159 days.

(21) Appl. No.: 11/409,415

(22) Filed: Apr. 21, 2006

(65) Prior Publication Data
US 2007/0012627 A1 Jan. 18, 2007

Related U.S. Application Data

(62) Division of application No. 10/761,816, filed on Jan. 20, 2004, now abandoned.

(60) Provisional application No. 60/440,949, filed on Jan. 17, 2003.

(51) Int. Cl.
 *B01D 15/08* (2006.01)
(52) U.S. Cl.
 USPC ...... 210/198.2; 210/635; 210/656; 210/502.1
(58) Field of Classification Search
 USPC ............................ 210/198.2, 635, 656, 502.1
 See application file for complete search history.

(56) References Cited

U.S. PATENT DOCUMENTS

| | | | |
|---|---|---|---|
| 4,810,456 A | 3/1989 | Bente, III et al. | 264/510 |
| 4,865,706 A | 9/1989 | Karger et al. | 204/182.8 |
| 5,316,680 A | 5/1994 | Frechet et al. | 210/635 |
| 5,431,807 A | 7/1995 | Frechet et al. | 210/198 |
| 5,593,729 A | 1/1997 | Frechet et al. | 427/337 |
| 5,633,290 A | 5/1997 | Frechet et al. | 521/54 |
| 5,929,214 A | 7/1999 | Peters et al. | 530/417 |
| 6,398,962 B1 * | 6/2002 | Cabrera et al. | 210/635 |
| 6,664,305 B2 * | 12/2003 | Jungbauer et al. | 521/64 |
| 6,749,749 B2 | 6/2004 | Xie et al. | 210/198.2 |
| 6,887,384 B1 | 5/2005 | Frechet et al. | 210/634 |
| 7,425,700 B2 * | 9/2008 | Stults et al. | 250/288 |

(Continued)

FOREIGN PATENT DOCUMENTS

EP          0 272 925          12/1987

OTHER PUBLICATIONS

Jia-Li Liao et al., "Preparation of Continuous Beds Derivatized with One-Step Alykl and Sulfonate Groups for Capillary Electrochromatography", Anal. Chem, vol. 68, pp. 3468-3472 (1996).

(Continued)

*Primary Examiner* — Ernest G Therkorn

(74) *Attorney, Agent, or Firm* — McLane, Graf, Raulerson & Middleton, PA

(57) ABSTRACT

A method of preparing an ultra-nanoscale-LC monolithic separation medium for use in capillary columns, or channels in microfabricated devices (microchips), and capillaries prepared by the method are disclosed. The application of moderate positive pressure to both ends of the capillary during the monolith polymerization process permits the preparation of monolithic capillary columns having very low i.d., e.g., 25 µm and smaller, with enhanced mass transfer properties and low back pressures, and excellent column-to-column reproducibility of retention times.

4 Claims, 17 Drawing Sheets

(56) References Cited

U.S. PATENT DOCUMENTS

| | | | |
|---|---|---|---|
| 7,582,214 B2* | 9/2009 | Brook et al. | 210/656 |
| 2002/0043499 A1* | 4/2002 | Hammen et al. | 210/656 |
| 2002/0088753 A1* | 7/2002 | Huber et al. | 210/656 |
| 2003/0062310 A1* | 4/2003 | Zare et al. | 210/656 |
| 2003/0230524 A1* | 12/2003 | Soga et al. | 210/198.2 |
| 2004/0101442 A1 | 5/2004 | Frechet et al. | 422/99 |
| 2004/0211730 A1* | 10/2004 | Zhang et al. | 210/656 |
| 2005/0023456 A1 | 2/2005 | Frechet et al. | 250/288 |
| 2006/0000773 A1* | 1/2006 | Glennon et al. | 210/635 |

OTHER PUBLICATIONS

Herve Cottet et al., "Heart-Cutting Two-Dimensional Electrophoresis in a Single Capillary", J. of Chromotography, vol. 1051, pp. 25-32, (2004).

S. Xie et al., "Rapid reversed-phase separation of proteins and peptides using optimized moulded monolithic poly(styrene-co-divinylbenzene)", Journal of Chromatography A, 865 (1999) pp. 169-174.

Tennikov et al., "Effect of porous structure of macroporous polymer supports on resolution in high-performance membrane chromatography of proteins", Journal of Chromatography A, 798 (1998) pp. 55-64.

Rohr et al., "Photografting and Control of Surface Chemistry in Three-Dimensional Porous Polymer Monoliths", Macromolecules 2003, 36, pp. 1677-1684.

Petro et al., "Molded continuous poly(styrene-co-divinylbenzene) rod as a separation medium for the very fast separation of polymers Comparison of the chromatographic properties of the monolithic rod with columns packed with porous and non-porous beads in high-performance liquid chromatography of polystyrenes", Journal of Chromatography a, 752 (1996) pp. 59-66.

Huang et al., "Surface' Alkylated Polystyrene Monolithic Columns for Peptide Analysis in Capillary Liquid Chromatography—Electrospray Ionization Mass Spectrometry", Anal. Chem, 2002, 74, pp. 2336-2344.

Svec et al., "Temperature, a Simple and Efficient Tool for the Control of Pore Size Distribribution in Macroporous Polymers", Macromolecules 1995, 28, pp. 7580-7582.

Stadalius et al., "Optimization model for the gradient elution separation of peptide mixtures by reversed-phase high-performance liquid chromatography", Journal of Chromatography, 296 (1984) pp. 31-59.

Wilm et al., "Electrospray and Taylor-Cone theory, Dole's beam of macromolecules at last?", International Journal of Mass Spectrometry and Ion Process 137 (19940 pp. 167-180.

Gale et al., "Small Volume and Low Flow-Rate Electrospray Ionization Mass Spectrometry of Aqueous Samples", Rapid Communications in Mass Spectrometry, vol. 7, pp. 1017-1021 (1993).

John B. Fenn, "Ion Formation from Charged Droplets: Roles of Geometry, Energy, and Time", American Society for Mass Spectrometry, 1993, pp. 524-535.

Zhang et al., "Capillary electrochromatography of proteins and peptides with a cationoc acrylic monolith", Journal of Chromatography A, (2000) pp. 465-477.

Wu et al., "An approach to the proteomic analysis of a breast cancer cell line (SKBR-3)", Proteomics 2003, pp. 1037-1046.

Wu et al., Practical aspects of ultrahigh pressure capillary liquid chromatography A. 911 (2001) pp. 1-12.

Valaskovic et al., "Attomole Protein Characterization by Capillary Electrophoresis-Mass Spectrometry", Science, vol. 273, pp. 1199-1202, Aug. 1996.

Shen et al., "High-Efficiency Nanoscale Liquid Chromatography Coupled On-Line with Mass Spectrometry Using Nanoelectrospray Ionization for Proteomics", Analytical Chemistry, vol. 74, No. 16, Aug. 15, 2002, pp. 4235-4249.

Premstaller et al., "High Performance Liquid Chromatography—Electrospray Ionization Mass Spectrometry Using Monolithic Capillary Columns for Proteomic Studies", Analytical Chemistry, vol. 73, No. 11, Jun. 1, 2001, pp. 2390-2396.

Premstaller et al., "High-Performance Liquid Chromatography—Electrospray Ionization Mass Spectrometry of Single- and Double-Stranded Nucleic Acids Using Monolithic Capillary Columns", Analytical Chemistry, vol. 72, No. 18, Sep. 15, 2000, pp. 4386-4393.

Peters et al., "Molded Rigid Polymer Monoliths as Separation Media for Capillary Electrochromatography. 2. Effect of Chromatographic Conditions on the Separation", Analytical Chemistry, vol. 70, No. 11, Jun. 1, 1998, pp. 2296-2302.

Peng et al., "Evaluation of Multidimensional Chromatography Coupled with Tandem Mass Spectrometry (LC?LC-MS?MS) for Large-Scale Protein Analysis: The Yeast Proteome", Journal of Proteome Research, 2002,2, pp. 43-50.

Moore et al., "A Microscale Electrospray Interface Incorporating a Monolithic, Poly(styrene-divinylbenzene) Support for On-Line Liquid Chromatography/Tandem Mass Spectrometry Analysis of Peptides and Proteins", Analytical Chemistry, vol. 70, No. 23, Dec. 1, 1998, pp. 4879-4884.

Meyers et al., "Network modeling of the convective flow and diffusion of molecules absorbing in monoliths and in porous particles packed in a chromatographic column", Journal of Chromatography A, 852 (1999) pp. 3-23.

MacNair et al., "Ultrahigh-Press Reversed-Phase Capillary Liquid Chromatography: Isocratic and Gradient Elution Using Columns Packed with 1.0-μm Particles", Analytical Chemistry, vol. 71, No. 3, Feb. 1, 1999, pp. 700-708.

Licklider et al., "Automation of Nanoscale Microcapillary Liquid Chromatography—Tandem Mass Spectrometry with a Vented Column", Analytical Chemistry, vol. 74, No. 13, Jul. 1, 2002, pp. 3076-3083.

Haskins et al., "Capillary LC-MS$^2$ at the Attomole Level for Monitoring and Discovering Endogenous Peptides in Microdial;ysis Samples Collected In Vivo", Analytical Chemistry, vol. 73, No. 21, Nov. 1, 2001, pp. 5005-5014.

Gusev et al., "Capillary columns with in situ formed porous monolithic packing for micro high-performance liquid chromatography and capillary electrochromatography", Journal of Chromatography A, 855 (1999) pp. 273-290.

Goetzinger et al., "Characterizarion of high molecular mass linear polyacrylamide powder prepared by emulsion polymerization as a replaceable polymer matrix for DNA squencing by capillary electrophoresis", Electrophoresis 1998, pp. 242-248.

Enlund et al., "Capillary electrochromatography of hydrophobic amines on continuous beds", Electrophoresis 2001, 22, pp. 511-517.

Emmett et al., "Micro-Electrospray Mass Spectrometry: Ultra-High-Sensitivity Analysis of Peptides and Proteins", American Society for Mass Spectrometry 1994, 5, pp. 605-613.

Cech et al., "Predicting Electrospray Response from Chromatographic Retention Time", Analytical Chemistry, vol. 73, No. 2, Jan. 15, 2001, pp. 208-213.

Cech et al., "Relating Electrospray Ionization Responses to Nonpolar Character of Small Peptides", Analytical Chemistry, vol. 72, No. 13, Jul. 1, 2000, pp. 2717-2723.

Adam et al., "Comparative study of capillary electroendosmotic chromatography and electrically assisted gradient nano-liquid chromatography for the separation of peptides", Journal of Chematography A, 894 (2000) pp. 241-251.

Adam et al., "Towards the column bed stabilization of xolumns in capillary electroendosmotic chromatography Immobilization of microparticulate silica columns to a continuous bed", Journal of Chromatography A, 887 (2000) pp. 327-337.

Ishizuka, et al. "Performance of a Monolithic Silica column in a Capillary under Pressure-Driven and Electrodriven Conditions" Analytic Chemistry, vol. 72 (2000) pp. 1275-1280.

* cited by examiner

FIG. 1A  FIG. 1B

SEQUENCE LISTING

<160> NUMBER OF SEQ ID NOS: 6

<210> SEQ ID NO 1
<211> LENGTH: 15
<212> TYPE: PRT
<213> ORGANISM: Bos taurus

<400> SEQUENCE: 1

Leu Gly Pro Asn Tyr Leu Gln Ile Pro Val Asn Cys Pro Tyr Arg
1               5                   10                  15

```
<210> SEQ ID NO 2
<211> LENGTH: 14
<212> TYPE: PRT
<213> ORGANISM: Bos taurus

<400> SEQUENCE: 2

Ile Gln Ala Leu Leu Asp Lys Tyr Asn Glu Glu Lys Pro Lys
 1               5                  10

<210> SEQ ID NO 3
<211> LENGTH: 13
<212> TYPE: PRT
<213> ORGANISM: Bos taurus

<400> SEQUENCE: 3

Asp Ala Leu Leu Phe Pro Ser Phe Ile His Ser Gln Lys
 1               5                  10

<210> SEQ ID NO 4
<211> LENGTH: 16
<212> TYPE: PRT
<213> ORGANISM: Bos taurus

<400> SEQUENCE: 4

Gly Ala Gly Ala Phe Gly Tyr Phe Glu Val Thr His Asp Ile Thr Arg
 1               5                  10                  15

<210> SEQ ID NO 5
<211> LENGTH: 19
<212> TYPE: PRT
<213> ORGANISM: Bos taurus

<400> SEQUENCE: 5

Gly Pro Leu Leu Val Gln Asp Val Val Phe Thr Asp Glu Met Ala His
 1               5                  10                  15

Phe Asp Arg

<210> SEQ ID NO 6
<211> LENGTH: 19
<212> TYPE: PRT
<213> ORGANISM: Bos taurus

<400> SEQUENCE: 6

Val Trp Pro His Gly Asp Tyr Pro Leu Ile Pro Val Gly Lys Leu Val
 1               5                  10                  15

Leu Asn Arg
```

NARROW I.D. MONOLITHIC CAPILLARY COLUMNS FOR HIGH EFFICIENCY SEPARATION AND HIGH SENSITIVITY ANALYSIS OF BIOMOLECULES

CROSS REFERENCE TO RELATED APPLICATIONS

This application is a divisional application of U.S. application Ser. No. 10/761,816 filed Jan. 20, 2004, now abandoned, which claims the benefit under 35 USC §119(e) of Provisional Application No. 60/440,949, filed Jan. 17, 2003, the whole of which are hereby incorporated by reference herein.

STATEMENT REGARDING FEDERALLY SPONSORED RESEARCH OR DEVELOPMENT

Part of the work leading to this invention was carried out with United States Government support provided under a grant from the National Institutes of Health, Grant No. GM 15847. Therefore, the U.S. Government has certain rights in this invention.

BACKGROUND OF THE INVENTION

The high mass sensitivity identification and quantitation of large numbers of peptides from protein digests is a major goal in proteomics. Nanoflow liquid chromatography, using commercially available 75 and 100 µm i.d. reversed phase columns, offers the advantages of high resolution, high mass sensitivity and low sample and mobile phase consumption. However, analysis of a limited amount of sample (e.g., tumor biopsy, laser capture microdissected cells, immunoprecipitated proteins, 2-D gel spots, etc.) can still be challenging with the above columns. For a fixed limited amount of sample injected, columns with smaller inner diameter can decrease chromatographic band dilution (Novotny et al., 1985; Haskins et al., 2001; and Unger, 1990) and thus increase the signal for concentration-sensitive ESI-MS (Shen et al., 2000). However, narrow bore columns (particularly those having less than 50 µm i.d.) are difficult to pack with conventional microparticles of 1-5 µm because of the very high pressure required to overcome the low column permeability due to the narrow bore (Shen et al., 2000; MacNair et al., 1999; and Wu et al., 2001).

A monolithic separation medium is made of a continuous, rigid, porous polymeric rod. Typically, prior art polymeric monolithic capillary columns for nano-LC and CEC separations, such as are disclosed in U.S. Patent Application No. US 2002/0088753 (Huber et al., 2002), which is hereby incorporated by reference herein, have been made in capillaries having inner diameters larger than 100 µm (Premstaller et al., 2001; Premstaller et al., 2000; Svec et al., 1995; Tennikov et al., 1998; Petro et al., 1996; Moore et al., 1998; Adam et al., 2000 (a); Adam et al., 2000 (b); and Enlund et al., 2001). Several approaches for synthesis of polymeric monoliths in capillaries of 100-300 µm i.d. have been published in which the reaction mixture is placed in the capillary, followed by UV- or thermally-induced in situ polymerization (Premstaller et al., 2001; Huang et al., 2002; Xie er al., 1999, Moore et al., 1998; Petro et al., 1996; Myers et al., 1999; and Rohr et al., 2003). High efficiencies are found, using the narrow bore capillary columns that have been made, due to decreased flow dispersion and a homogeneous packing bed structure. However, it would be very desirable to be able to extend those advantages consistently to significantly more narrow i.d. columns, particularly to those having i.d. values of 25 µm or less.

BRIEF SUMMARY OF THE INVENTION

The present invention relates to an ultra-nanoscale-LC monolithic separation medium for use in capillary columns or channels in microfabricated devices (microchips). Surprisingly, it was found that applying moderate pressure to both ends of the capillary during the monolith polymerization process permits the preparation of monolithic capillary columns having very low i.d., e.g., 25 µm and smaller, with enhanced mass transfer properties and low back pressures which can be operated with significantly lower pressures than packed bed columns of the same i.d.

Thus, in one aspect, the invention is directed to a method of preparing a separation capillary column, or channel in a microfabricated device, that includes a polymeric monolithic separation medium. The method comprises the steps of providing an unfilled capillary column or channel, the column or channel being open at both ends thereof, the inner surface of the column or channel being suitable for covalent attachment of a polymeric monolithic separation medium; adding to the column or channel a degassed polymerization mixture that includes monomer, crosslinking agent and inert porogens; polymerizing the mixture in the presence of an initiator in the column or channel, during which polymerization, the mixture is continuously maintained under positive pressure applied from the open ends of the column or channel; and following the polymerization step, washing the rigid polymeric monolithic separation medium so formed inside the column or channel to remove the porogens and any remaining polymerization mixture.

A separation capillary column, or channel in a microfabricated device, according to the invention includes a monolithic separation medium comprising a macroporous, rigid, continuous polymeric structure, the polymeric structure being attached covalently to the wall of the column or channel, wherein the column or channel has an i.d. of 25 µm or less, wherein the efficiency of operation of the column or channel is greater than 100,000 theoretical plates per meter and wherein the reproducibility of retention time on comparable columns or channels during use varies less than 10%.

The separation medium according to the invention is easy to manufacture reproducibly and can be made more permeable than comparable packed bed columns. This medium is useful particularly for high sensitivity mass spectrometry analysis of biomolecules. Columns or microchips according to the invention can be used for analysis of biomolecules at a level around 5-10 attomoles, or even around one attomoles, when coupled to an appropriate analysis system, e.g., electrospray ionization quadropole ion trap mass spectrometry (ESI-MS).

BRIEF DESCRIPTION OF THE DRAWINGS

Other features and advantages of the invention will be apparent from the following description of the preferred embodiments thereof and from the claims, taken in conjunction with the accompanying drawings, in which:

FIGS. 1A and 1B are scanning electron micrographs showing cross-sectional views of monolithic packing thermally polymerized according to the invention, at 5,000× and 12,500× magnification, respectively;

FIG. 3A is a 3-D overlay of an LC-MS chromatogram; FIG. 3B is a planar ion density map; and FIG. 3C shows extracted ion chromatograms for selected peptides of the tryptic digest of the 10-protein mixture;

FIG. 5A shows extracted ion chromatograms for selected peptides, and FIG. 5B shows spectra at the peak maximum of the same peptides;

FIG. 7A shows extracted ion chromatograms for selected peptides, and FIG. 7B shows a spectrum at peak maximum of the catalase tryptic peptide LGPNYLQIPVNCPYR (SEQ ID NO: 1);

DETAILED DESCRIPTION OF THE PREFERRED EMBODIMENT OF THE INVENTION

Figure 1C:
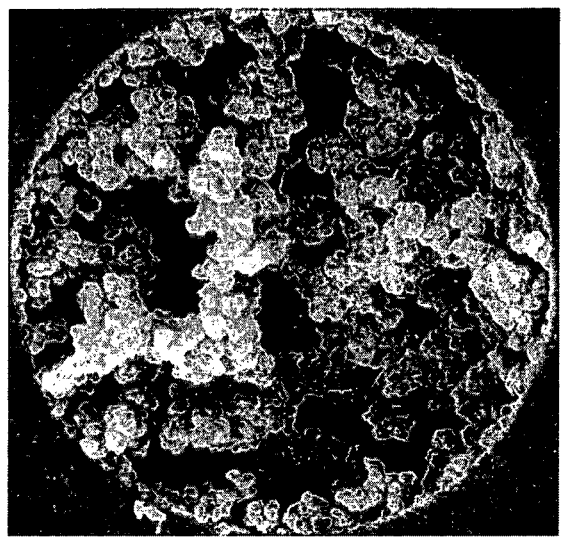
FIG. 1C is a perspective view of a section of a typical capillary column containing monolithic packing according to the invention.
Figure 1C:
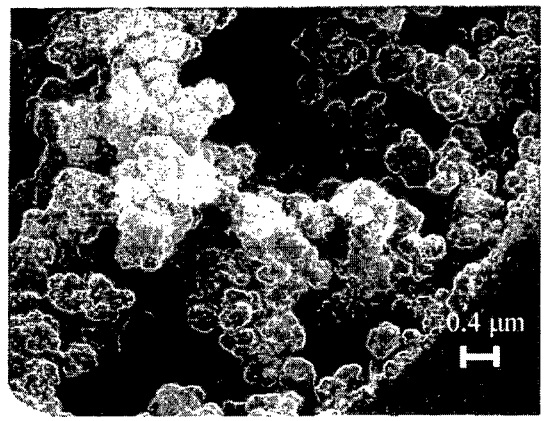
Figure 1C:
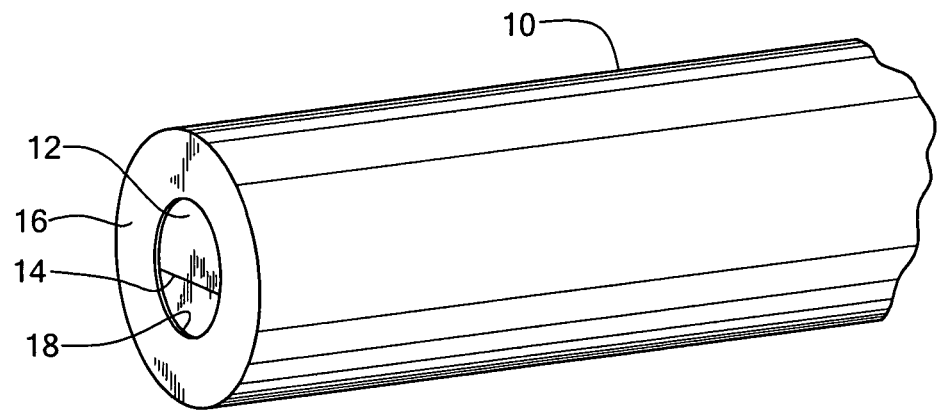

A monolithic separation medium prepared as described herein results in monolithic capillary columns having very low i.d., e.g., 25 μm and smaller, with enhanced mass transfer properties and relatively low back pressures Such columns can be made more permeable than comparable packed bed columns and, thus, have the potential to run with less applied pressure. Columns according to the invention have an efficiency of operation of greater than 100,000 theoretical plates per meter. Furthermore, the reproducibility of the retention time of a standard compound on comparable columns prepared by the method of the invention varies less than 10%.

The major advantages of the current invention over other approaches for preparing monolith or particulate capillary columns include high mass ensitivity for ESI-MS analysis of biomolecules at the low attomole level using the current generation of ion trap mass spectrometers (e.g., LCQ Deca XP+, ThermoFinnigan); the potential for higher permeability than comparable packed bed (or particulate) columns; high efficiency in the pressure-driven elution mode; ease of manufacture in comparison to particulate columns with the same dimensions; less ESI tip clogging problems, which are common in the use of particulate columns; better durability, because monoliths do not need frits; and good column-to-column and run-to-run reproducibility.

The high efficiency of narrow i.d. capillary monolithic columns according to the invention is due to flowing within the packing structure during operation and a very homogeneous packing bed structure, in which the stabilizing influence of the wall is felt by the entire packing bed. The bulk liquid flow in very narrow i.d. capillary columns is considerably reduced relative to 75-100 μm i.d. columns, which means that the analytes are dissolved in much less eluent, resulting in higher concentration sensitivity, ease in coupling to ESI mass spectrometry and higher electrospray ionization ability. Such columns provide capability for desalting, preconcentration on the head of the column and separation of biomolecules. The columns provide a wide linear dynamic range, i.e., no band broadening problems. The column loading capacity is described in terms of the maximum injection amount that can be loaded onto the separation column without the appearance of peak broadening. Columns according to the invention provide a loading dynamic range that is competitive with the dynamic range of a particulate column, retaining linearity over a range of orders of magnitude of 3.5 or greater.

The relatively low backpressure in monoliths for a given column i.d. and polymeric quasi-bead (or pseudo-bead) size is a result of increased porosity. Even monolithic columns with very low i.d. (10-20 μm) provide relatively low backpressure, which makes it possible to operate these columns with common LC equipment and bearable elution delay time. Thus, monolithic analogues to narrow i.d. particulate columns packed with beads of a size of even 1 μm or less are possible to make. The monolith columns according to the invention with pseudobeads smaller than 1 μm demonstrate high efficiency and loading capacity as well as reasonable backpressure.

The process of producing columns (or channels in microfabricated devices) according to the invention comprises: a) adding to a narrow i.d. fused silica capillary or a narrow i.d. channel im a microchip (e.g., 25 μm and smaller) with treated inner wall, a degassed polymerization mixture containing monomer, crosslinker and inert porogens; 2) polymerizing the mixture in the presence of initiator in the capillary or channel while pressurized from both ends to form a macroporous, rigid, continuous, uniform structure attached to the wall of the capillary; and 3) washing the rigid structure that has been formed with a solvent to remove the porogens and remaining polymerization mixture.

The polymerization mixture contains a suitable monomer or monomers with appropriate amounts of suitable crosslinker. Polymerization and crosslinking (e.g., by thermal or photopolymerization) in the presence of porogens lead to a phase separation during the ongoing polymerization reaction and effect the formation of permanent channels in the material (Petro et al., 1996; Enlund et al., 2001; and Seidl et al., 1967). In a preferred embodiment according to the invention, styrene was chosen as a monomer, tetrahydrofuran (THF) and n-octanol were chosen as inert porogens, and divinylbenzene (DVB) was the crosslinker. α,α'-Azobisbutyronitrile (AIBN) served as radical initiator. Other suitable crosslinkable monomers include the methacrylates. In general, any polymerization mixture component used by those of skill in the art for the preparation of prior art monolith columns, e.g., those of 75-100 μm i.d. or greater, can be used in this invention. As mentioned, the resulting monolith was covalently attached to the inner wall of the capillary. Such immobilization helps to avoid shrinkage of the monolith during polymerization and eliminates the necessity of retaining frits.

Published procedures for column polymerization were not found to be successful for low i.d. capillaries (Premstaller et al., 2001; Premstaller et al., 2000; Svec et al., 1995; Petro et al., 1996; and Moore et al., 1998). Polymerization of monoliths narrower than 50 μm i.d. without column pressurization led to the appearance of gaps and dramatic shrinkage of the polymer due to the narrow i.d. capillaries and the higher surface-to-volume ratio. However, the application of positive pressure during polymerization, according to the method of the invention, minimizes monolith structure irregularities that occur in making porous monoliths in capillaries narrower than 50 μm i.d. For example, the application of mild pressurization (e.g., 30-60 psi) from both ends of a 20-25 μm i.d. capillary filled with polymerization mixture resulted in a uniform continuous monolithic structure after polymerization. In addition, the synthesis of polymeric monolithic nano-LC columns with, e.g., 10-15 μm i.d. and narrower is also achievable using this method. Further adjustment of applied pressure and polymerization mixture composition can be made, if needed. A lower pressure, e.g., 10-20 psi, can be used during polymerization in somewhat wider columns, e.g., 40-50 μm, and a higher pressure, e.g., 75-150 psi, is needed for polymerization in a very narrow column, e.g., 10-15 μm and narrower. Pressurization during the polymerization process, according to the invention, provides the potential for column-to-column and batch-to-batch reproducibility of the resulting monolith separation medium.

The exact adjustment of polymerization conditions is important for the preparation of high performance monoliths according to the invention in the same way that it is important for prior art monoliths in, e.g., 75-100 μm i.d. columns. These conditions include use of the inert porogens, which are soluble or at least miscible with monomers. Careful control of the polymerization kinetics is also important for the morphology of the monolith. Temperature, reaction time and polymerization mixture composition affect the performance of the monolith as well. The most important parameters for the construction of a specific pore size are monomer type, solubility and reactivity, amount of crosslinker, amount and type of porogens, solubility of porogens for polymer, polymerization temperature and pressure (Svec et al., 1995; Petro et al., 1996; and Seidl et al., 1967). With a careful controlled polymerization process, the middle sections of a longer synthesized monolithic capillary column will be identical in performance characteristics to sections at either end of the column.

The resulting polymeric monolith contains relatively large channels that allow rapid convective mass transport between the mobile phase and the layer of polymer (i.e., rapid flow through). Scanning electron micrographs were acquired to characterize the column morphology and surface structure of a typical column according to the invention. FIGS. 1A and 1B are cross-sectional views of monolithic packing polymerized according to the invention, as described in Example I, at 5000× and 12,500× magnification, respectively.

A summary example of column performance parameters is as follows: (1) geometry: 20 μm i.d., 360 μm o.d.×10 cm in length; (2) flow rate: 10-55 nL/min; (3) backpressure: 50-150 bars; (4) efficiency: 250,000 theoretical plates/meter; (5) reproducibility (RSD for retention time): less than 1%; (6) LOD in ESI-MS, ESI-MS/MS: 1-10 amol; (7) linear dynamic range in ESI-MS: 100 fg-500 pg (3.5 orders of magnitude)— in some cases, over 4-5 orders of magnitude have been observed. Column-to-column reproducibility on comparable columns during use generally varied less than 10% and frequently less than 4%.

The following examples are presented to illustrate the advantages of the present invention and to assist one of ordinary skill in making and using the same. These examples are not intended in any way otherwise to limit the scope of the disclosure.

Materials and Methods

Materials.

Fused-silica capillary tubing (20 μm i.d., 360 μm o.d.), with a polyimide outer coating, was purchased from Polymicro Technologies (Phoenix, Ariz.). Divinylbenzene, styrene, n-octanol, tetrahydrofuran (THF), 2,2'-azobisisobutyronitrile (AIBN), sodium hydroxide, hydrochloric acid, vinyltrimethoxysilane, formic acid and isopropanol were obtained from Aldrich (Milwaukee, Wis.). Sequencing-grade TPCK-treated trypsin and standard peptides and proteins were obtained from Sigma (St. Louis, Mo.) and HPLC-grade methanol and acetonitrile from Fisher (Fair Lawn, N.J.). Deionized water (18.2 MΩ) was prepared using a Milli-Q system from Millipore (Bedford, Mass.).

Column Pretreatment.

Pretreatment and vinylization of the fused-silica capillaries were based on a previously published procedure[21]. In brief, capillaries 50 cm long were flushed with 0.5 M sodium hydroxide for 30 min and then washed with deionized water for 5 min, followed by methanol for 5 min. Next, the inner surface of the fused-silica capillaries was treated with vinyltrimethoxysilane to attach covalently the anchoring vinyl sites for the grafting of the polymeric stationary phase. Capillaries were then rinsed for 40-50 min with a solution consisting of 0.36 M hydrochloric acid and 14.3% (v/v) of methanol in vinyltrimethoxysilane. The rinsing solution was mixed and degassed by ultrasonication for 5 min before use. Subsequently, the capillaries were continually purged with helium for 1 hour at 100° C.

Tryptic Protein Digestion.

Proteins (cytochrome c (hourse), trypsinogen (bovine), myoglobin (horse), serum albumin (bovine), ovalbumin (chicken), β-casein (bovine), α1-acid glycoprotein (human), β-lactoglobulin (bovine), α-lactoglobulin (human) and catalase (bovine)) were dissolved in 1 mL of 6 M guanidine chloride, 50 mM Tris HCl (pH 8.0), 5 mM DTT and incubated for 1 hour at 60° C. for denaturation and reduction. Then, an aliquot of protein solution was diluted ten fold by 50 mM ammonium bicarbonate pH 8.0 at a concentration of ~1 mg/mL. Trypsin was added at a substrate-to-enzyme ratio of 100:1, and the solution was incubated overnight at 37° C. The digest was vacuum-dried and reconstituted in water without additional clean-up steps before analysis.

Mass Spectrometry.

An LCQ Deca XP+ quadrupole ion trap mass spectrometer (ThermoFinnigan, San Jose, Calif.) was used in all experiments. On-line ESI-MS was performed in the positive-ion mode with the ESI voltage set at 0.5-1.4 kV and the heated inlet capillary maintained at 160° C. All nano-LC-MS experiments were carried out with a maximum in-source sample injection time of 50 ms, and three microscans were summed for each scan. In all data dependent MS/MS experiments, a full MS scan between 400 and 2000 m/z was followed by three full MS/MS scans for the three most intense ions. The relative collision energy was set to 35%, with an activation time of 30 ms. Dynamic exclusion was used with a repeat count of 2 and a repeat duration of 1 minute, with a three-minute exclusion duration window. The activation time was set at 30 ms, the default charge state of +2 and an isolation width of 3 m/z. The results of data dependent MS/MS scanning were submitted for a search against a database created for the selected model proteins and the nonredundant protein database nr.fasta using the TurboSequest algorithm (Bioworks 3.0, ThermoFinnigan).

Nano-LC-ESI-MS.

An UltiMate™ Micro Pump (Dionex, Sunnyvale, Calif.) equipped with an Accurate™ Stream Splitter was used to deliver mobile phase through the column. The monolithic nanocapillary column was attached to a manual injector, VICI Model C4-0004-.01 with a 10 nL or 200 nL internal loop (Valco Instruments Co., Houston, Tex.). ESI voltage (+0.5 to +1.4 kV) was applied to the inlet of the column at the injector.

A simple design of a sheathless electrospray emitter was used to produce a stable spray. The outlet of the monolithic column was connected as close as possible to a spray capillary (20 μm I.D., 365 μm O.D., 5 μm tip orifice I.D., 1.5-2 cm, New Objective, Mass.) butt-to-butt, and the connection was held together with Teflon tubing (250 μm I.D., 1.6 mm O.D., 1.5 cm) (Dionex). The estimated dead volume was calculated to be less than 5 nL. The ends of all capillaries were ground by a fine diamond sand lapper (VWR Scientific Products, West Chester, Pa.) before use. The position of the ESI emitter was carefully optimized within a distance of 0.3-1 mm to the mass spectrometer inlet orifice with use of a micromanipulator for maximum signal intensity.

EXAMPLE I

Preparation of Low I.D. Monolithic Columns with Thermal Polymerization

The general procedure for producing monolithic columns according to the invention in this example consists of: 1) covalent modification of the fused silica capillary inner wall by vinyltrimethoxysilane; 2) filling the narrow i.d. capillary with a degassed polymerization mixture containing monomer, crosslinker and inert porogens; 3) thermally-induced in situ polymerization in the presence of initiator in a capillary pressurized from both ends to form a macroporous, rigid, and uniform structure covalently attached to the capillary inner surface; and 4) washing out the porogens and remaining polymerization mixture. Polymerization and crosslinking led to a phase separation to create permanent channels in the rigid polymeric material. The composition of the polymerization mixture was related to earlier studies (Premstaller et al., 2001; Petro et al., 1996; Enlund et al., 2000; Seidl et al., 1967; and Zhang et al., 2000) but was carefully optimized to achieve high chromatographic performance. Covalent immobilization helped reduce shrinkage of the monolith during the polymerization (Premstaller et al., 2001) and eliminated the need for retaining frits. Either thermal or UV-initiated polymerization could be used for synthesis of the monoliths in capillaries (zhang et al., 2000; and Peters et al., 1998). Typically, heat-induced polymerization is a longer process (Premstaller et al., 2001; Petro et al., 1996; Enlund et al., 2000; Seidl et al., 1967; Zhang et al., 2000; and Peters et al., 1998), but it was chosen here since 20-μm i.d. fused silica tubing with a UV-transparent outer coating was not commercially available at the time of this experiment.

The specific procedure for preparation of these columns was as follows. After column pretreatment as described above, a polymerization mixture containing 16.5% (v/v) styrene, 16.5% (v/v) divinylbenzene, 7.9% (v/v) THF, 59.1% (v/v) n-octanol and 1% (w/v) AIBN was prepared, followed by filtering using a single-use syringe with an 0.02 μm Millipore PVDF filter (Bedford, Mass.). The solution was degassed (air removal) by ultrasonication for 5 min, and then the vinylsilanized capillaries were filled with the polymerization mixture. Separate tests revealed similar column performance for helium degassing as for ultrasonication for the small volume of the polymerization mixture of 2.4 mL. Both ends of the capillary were immersed in a 4-mL vial half-filled with the polymerization mixture and sealed by a screw cap with two silicon rubber septa (Alltech Associates, Inc., Deerfield, Ill.). The vial was pressurized (30-40 psi) with helium, and the vial with the capillary was heated in a GC oven at 75° C. for 3 h, then 85° C. for another 16 h. Next, 3-5 cm long column sections were removed from both ends of the capillary, and the column was purged with nitrogen, washed with methanol and purged again with nitrogen to eliminate any remaining polymerization solution. The capillary was cut into 10 cm long pieces, and the column was then ready for use. The column was stored in a dry state before and after use.

Standard procedures (Premstaller et al., 2001; Moore et al., 1998; Petro et al., 1996; and Svec, 1995) for column polymerization in low i.d. capillaries were not found to be successful. Polymerization of monoliths narrower than 50-μm i.d. without column pressurization led to the appearance of gaps and a dramatic shrinkage of the polymer structure due to the fast kinetics of the exothermic polymerization reaction in the narrow i.d. capillaries together with the relatively high surface-to-volume ratio. Pressurization during polymerization (Bente et al., 1998) reduced monolith structure irregularities by both minimizing shrinkage (Bente et al., 1998 and Huber et al., 2002) and bubble formation with porous monoliths in the 20-μm i.d. column. Typically, 40-50 psi applied from both ends of the capillary filled with polymerization mixture helped to achieve a uniform continuous monolithic structure. Not being bound by any theory, it appears that constant pressurization during polymerization supplies additional portions of the mixture of monomers, which compensated for shrinkage. Pressurization also has helped to improve column-to-column reproducibility and has enabled synthesis of 10 and 15 μm i.d., and narrower, polymeric monolithic nano-LC columns.

Careful optimization of the polymerization conditions was necessary for the preparation of high performance monoliths. Careful control of the polymerization kinetics was also important for the specific morphology of the monolith. Temperature, reaction time and polymerization composition all affected performance. A number of parameters were significant in producing a specific pore size including monomer type: solubility and reactivity, the amount of crosslinker, the amount and type of porogens, the solubility of polymer in porogens, polymerization temperature and pressure (Petro et al., 1996; Seidl, 1967; and Bente et al., 1989). The middle 25-40 cm sections of a longer (50-60 cm) synthesized monolithic nanocapillary column were found to be similar in chromatographic performance when the polymerization process was carefully controlled.

Figure 1D:
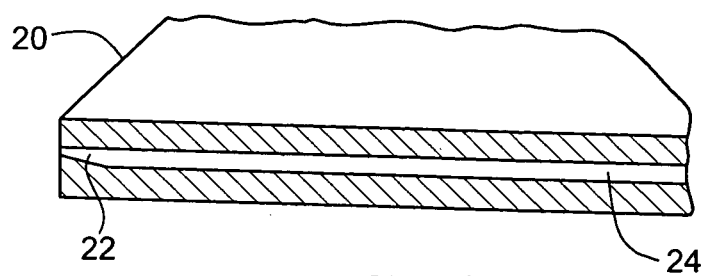
FIG. 1D is a cross-sectional view of a channel of a microchip containing monolithic packing according to the invention.

Scanning electron micrographs were acquired from ~1 cm long cuts of different column sections to examine the column morphology and surface structure. FIGS. 1A and 1B present scanning electron microscopy (SEM) images of the monolith, demonstrating a well-ordered polymeric quasi-bead structure with attachment to the capillary wall. The monolith contained relatively large flow-through channels (~1.5-3 μm) that allowed rapid convective mass transport between the mobile phase and surface of the polymer. The relatively low backpressure for monoliths for a given column i.d. and pseudo-bead size (~0.3-0.5 μm) at a typical flow rate of 20-50 nL/min was a result of this increased porosity. SEM images of different sections of the column appeared to be similar in structure. Referring to FIG. 1C, a typical column 10 has a fused silica outer wall section 16 with a narrow bore having an inner diameter (i.d.) 14. The monolith 12 is bonded covalently to the inner column wall 18 and so is retained within the narrow bore of the column. As shown in FIG. 1D, a microchip 20 according to the invention has a narrow channel 22, which contains the monolith. The exit end of the channel narrows down in this example to form an electrospray tip 24.

Example II

Performance Characterization of Thermally Polymerized Columns

Figure 2:
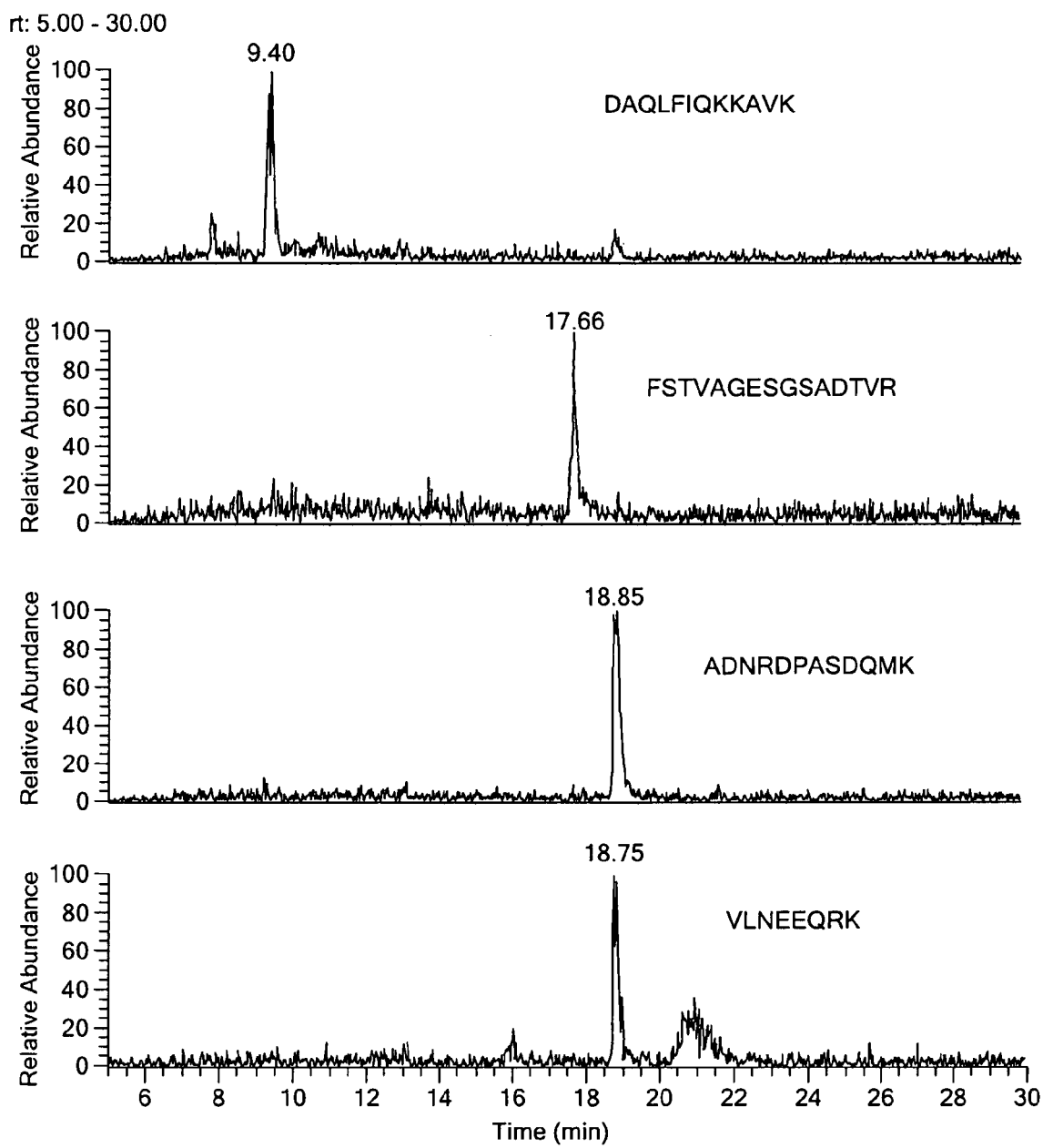
FIG. 2 shows extracted ion chromatograms for selected tryptic peptides for isocratic nano-LC-ESI-MS on a monolithic column according to the invention (e.g., 20 μm i.d.×10 cm)

A variety of chromatographic studies were conducted to characterize the 20 μm i.d. monolithic columns under isocratic conditions. The PS-DVB monolithic columns with pseudobeads smaller than 1 μm demonstrated high efficiency, over 100,000 plates/meter (calculated from extracted ion chromatograms) for peptides over a range of capacity factors (3≤k'≤10) using a 10 cm long column, with typical peak widths at half height of 5-15 s (FIG. 2), as well as reasonable backpressure of 50-150 bars. Specifically, FIG. 2 shows extracted ion chromatograms for selected tryptic peptides for isocratic nano-LC-ESI-MS on a monolithic column of 20 μm i.d.×10 cm (5 fmol injected on the column). Mobile phase: 15% (v/v) acetonitrile, 0.1% (v/v) formic acid in water. Flow rate: ~25 nL/min. Column backpressure: ~75 bars. Average efficiency exceeds 250,000 plates per meter. The peak widths at half of height ($W_{1/2}$): 12 s for DAQLFIQKKAVK, 6 s for FSTVAGESGSADTVR, 10 s for ADNRDPASDQMK and 9 s for VLNEEQRK.

Figure 3A:
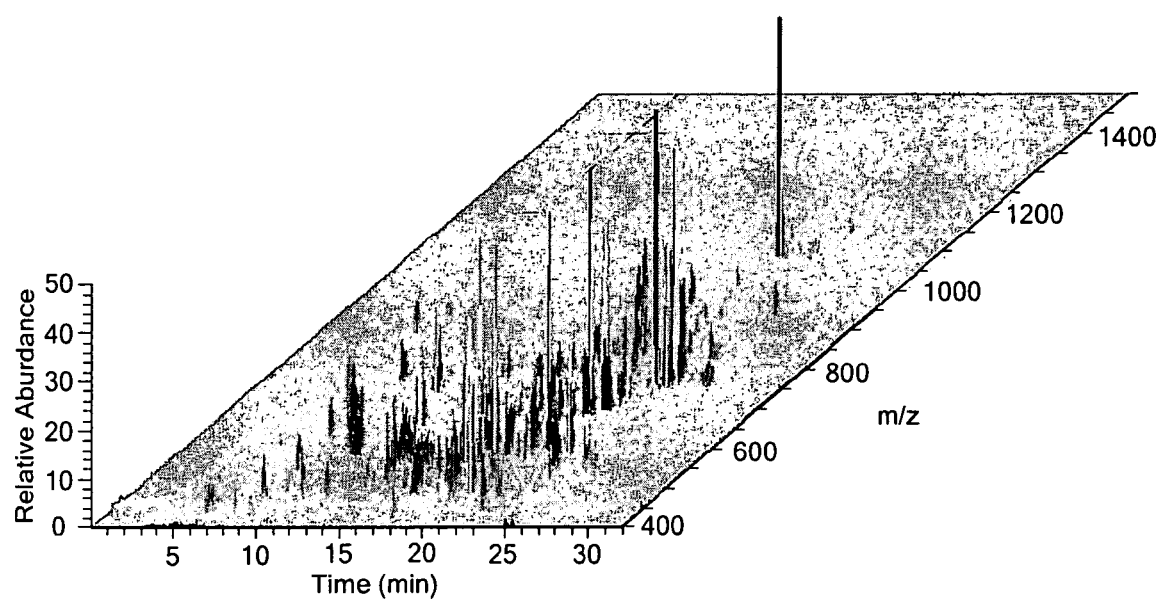
FIGS. 3A-3C show gradient nano-LC-ESI-MS of a tryptic digest of a 10-protein mixture on a monolithic column according to the invention.
Figure 3B:
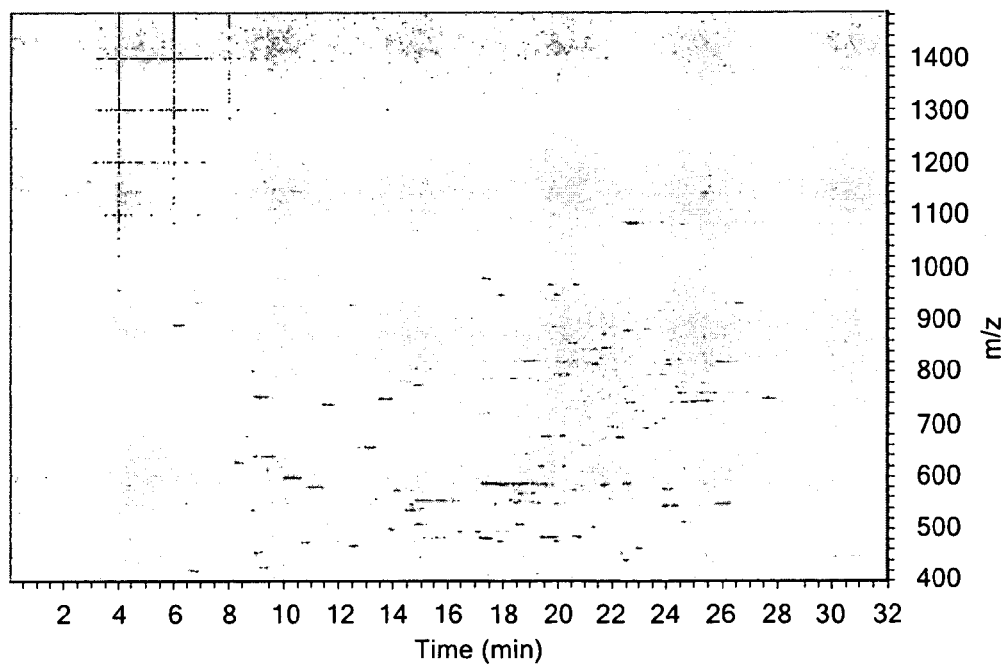
Figure 3C:
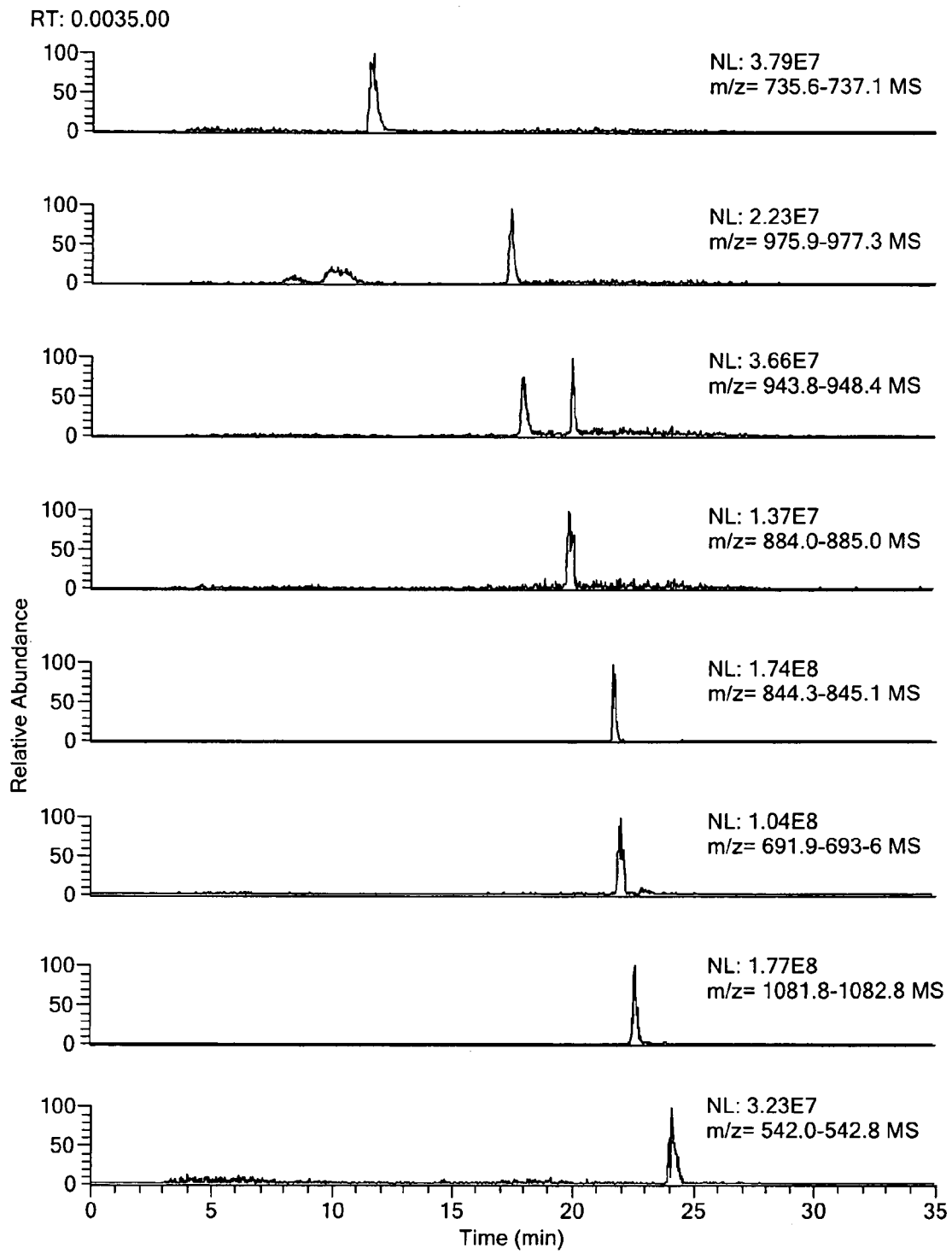

Demonstrating the resolving power of the 20-μm i.d. monolith, FIGS. 3A-3C show gradient nano-LC-ESI-MS analysis of a tryptic digest of a model 10-protein mixture containing hundreds of peptides at the level of 10-40 femtomoles. The protein mixture included cytochrome c (horse), trypsinogen (bovine), myoglobin (horse), serum albumin (bovine), ovalbumin (chicken), β-casein (bovine), α1-acid glycoprotein (human), β-lactoglobulin (bovine), α-lactoglobulin (human) and catalase (bovine). Separation with subsequent on-line ESI-MS was performed with a 30-minute gradient. (Column conditions—Mobile phase: solvent A: 2% (v/v) acetonitrile, 0.1% (v/v) formic acid in water; solvent B: 10% (v/v) water, 5% (v/v) isopropanol, 0.1% (v/v) formic acid in acetonitrile. Gradient: 5% B, 0 min; 40% B, 25 min; 90% B, 26 min; gradient steepness parameter b=0.28. Injection was made and data acquisition commenced 10 min after the start of the gradient.) A 3-D overlay of the LC-MS chromatogram (FIG. 3A) and a planar ion density map (FIG. 3B) demonstrate the complexity of the sample and the high resolving power of the method. FIG. 3C presents examples of extracted ion chromatograms for several peptides with typical narrow elution windows of 15-40 seconds (at the retention time 8≤$t_R$≤30 min). MS/MS data-dependent scanning followed by TurboSEQUEST searching against a database created for the selected model proteins allowed identification of all proteins in the mixture with a high score. The total number of fully tryptic peptides identified in a single run with 25 minute gradient was 96 with a SEQUEST delta correlation (ΔCn) greater than 0.08 and a correlation (Xcorr) greater than 2.0 and for singly charged ions, correlation (Xcorr) greater than 1.5 for doubly charged ions and Xcorr greater than 3.3 for triply charged ions (Peng et al., 2003).

Special attention was paid to system dead volumes. Pre-column dwell volume and post column dead volume were downscaled to ~200 nL and ~5 nL, respectively. Injection volumes were maintained below ~30% of the average eluting peak volume, as typical in HPLC, to avoid band broadening. In the gradient elution mode, this injection limitation can be overcome by preconcentration either at the head of the column or with a vented trapping column placed at the head of the separation column (Peng et al., 2003).

Figure 4:
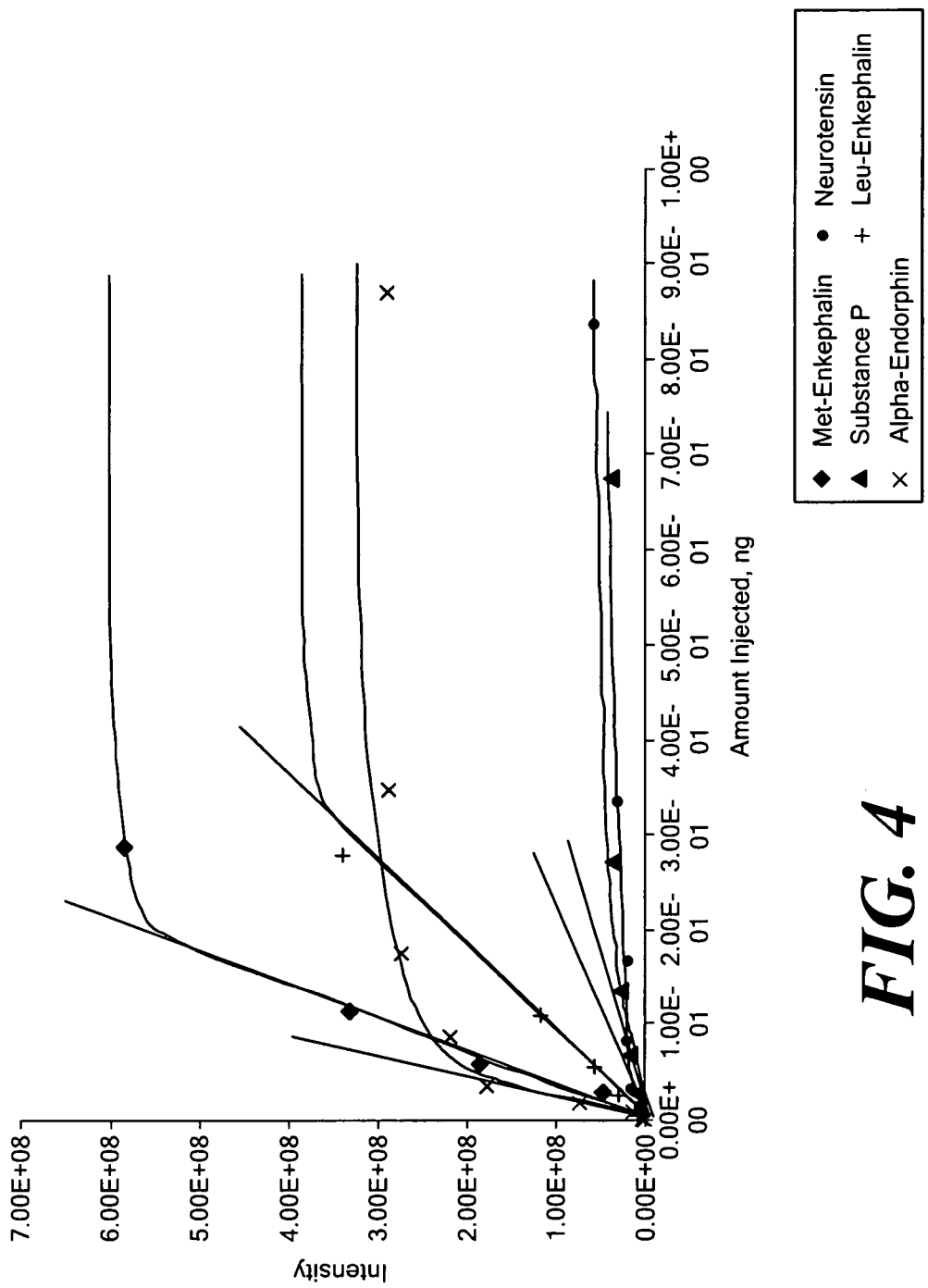
FIG. 4 is a graph showing the linearity of loading dynamic range measurements for a monolithic column according to the invention with a steep gradient.

The monolithic column provided a wide linear dynamic range of loading capacity, as described as the maximum injection amount without the appearance of increased peak broadening. For example, referring to FIG. 4, the monolithic column resulted in a linear dynamic mass range of 3.5 orders of magnitude (100 fg-500 pg) for small peptides ($M_w$ 555.6-1746.0, retention time 6≤$t_r$≤18 min) on the column under a sharp gradient (b=0.8, $t_g$=10 min) (see, Appendix for definitions). The model peptide mixture contained equal amounts from 1 amol to 10 pmol each of met-enkephalin (1, ♦), leu-enkephalin (2, +), α-endorphin (3, ×) and neurotensin (4, ●).

Peptides with higher retention (10≤$t_R$≤32 min) showed a linear dynamic range up to 4.5-5 orders of magnitude under shallower (b=0.42, $t_g$=20 min) gradient conditions. This linear dynamic range of ~4 orders of magnitude was found to be similar to that for a 75 μm i.d.×15 cm packed capillary column under similar gradient elution conditions (0.4≤b≤0.8), but the mass range shifted by ~20 fold towards the lower injected amounts for the 20 μm i.d. column.

Retention reproducibility of the monolithic columns was tested for the separation of tryptic peptides of a bovine catalase digest (see Tables 1, 2). Limited run-to-run and column-to-column repeatability studies were performed by measuring the relative standard deviation of peptide retention times from three independent sets of measurements. Run-to-run reproducibility was found to be better than 1% variation, and column-to-column (3 columns) reproducibility was generally better than 10% variation and most particularly better than 4% variation. The columns could be flushed with solvents in either direction up to at least 1200 psi pressure without any damage to the monolithic structure and could withstand prolonged exposure to mobile phases from pH 2.0 to pH 11.5 for at least several months (at least 1000 injections per column). As noted by others, clogged columns can be reused after cutting a short piece (~1-2 mm) from the clogged end or after grinding away the end of the column with a diamond sand lapper. Monolithic nanocapillary columns also resulted in less clogging of the ESI tip in comparison to packed columns because of the absence either of loose particles in the column bed or frits and also because of higher chemical stability.

TABLE 1

Run-to-run reproducibility for the retention time of the selected catalase tryptic peptides (100 amol of digest injected on the monolithic column).

| Tryptic Peptides of Catalase Digest | SEQ ID NO: | Retention time, min | | | | | |
|---|---|---|---|---|---|---|---|
| | | Run#1 | Run#2 | Run#3 | Average | Standard dev. | RSD |
| LGPNYLQIPVNCPYR m/z 903.5 | 1 | 28.48 | 28.15 | 28.36 | 28.33 | 0.17 | 0.59% |
| IQALLDKYNEEKPK m/z 563.2 | 2 | 29.68 | 29.26 | 29.46 | 29.47 | 0.21 | 0.71% |

TABLE 1-continued

Run-to-run reproducibility for the retention time of the selected catalase tryptic peptides (100 amol of digest injected on the monolithic column).

| Tryptic Peptides of Catalase Digest | SEQ ID NO: | Run#1 | Run#2 | Run#3 | Average | Standard dev. | RSD |
|---|---|---|---|---|---|---|---|
| DALLFPSFIHSQK m/z 750.2 | 3 | 29.68 | 29.33 | 29.51 | 29.51 | 0.18 | 0.59% |
| GAGAFGYFEVTHDITR m/z 582.3 | 4 | 26.87 | 26.51 | 26.68 | 26.69 | 0.18 | 0.67% |
| GPLLVQDVVFTDEMAHFDR m/z 731.1 | 5 | 38.16 | 38.08 | 38.08 | 38.11 | 0.05 | 0.12% |
| VWPHGDYPLIPVGKLVLNR m/z 1087.9 | 6 | 38.85 | 38.82 | 38.82 | 38.83 | 0.02 | 0.04% |

TABLE 2

Column-to-column reproducibility for the retention time of the selected catalase tryptic peptides (100 amol of digest injected on two different monolithic columns).

| Tryptic Peptides of Catalase Digest | SEQ ID NO: | Column #1 | | | Column #2 | | | RSD |
|---|---|---|---|---|---|---|---|---|
| | | Run#1 | Run#2 | Run#3 | Run#1 | Run#2 | Run#3 | |
| LGPNYLQIPVNCPYR m/z 903.5 | 1 | 28.48 | 28.15 | 28.36 | 27.53 | 29.53 | 28.47 | 2.28% |
| IQALLDKYNEEKPK m/z 563.2 | 2 | 29.68 | 29.26 | 29.46 | 28.57 | 30.21 | 28.94 | 1.95% |
| DALLFPSFIHSQK m/z 750.2 | 3 | 29.68 | 29.33 | 29.51 | 29.60 | 30.14 | 28.94 | 1.34% |
| GAGAFGYFEVTHDITR m/z 582.3 | 4 | 26.87 | 26.51 | 26.68 | 26.55 | 28.46 | 27.26 | 2.74% |
| GPLLVQDVVFTDEMAHFDR m/z 731.1 | 5 | 38.16 | 38.08 | 38.08 | | 35.52 | 35.60 | 3.76% |
| VWPHGDYPLIPVGKLVLNR m/z 1087.9 | 6 | 38.85 | 38.82 | 38.82 | 37.39 | 37.74 | 38.38 | 1.64% |

Example III

Mass Sensitivity of Nano-LC-ESI-MS Using 20 μm i.d. Monolithic Columns in Tryptic Peptide Analysis A main characteristic of nanocolumns is high mass sensitivity, as a result of the decreased dilution of the chromatographic band (Novotny et al., 1985; Haskins et al., 2001 and Unger et al., 1990). Theoretically, downscaling from conventional nano-LC columns of 75 μm i.d. to 20 μm i.d. should result in a gain in sensitivity of $(d_1/d_2)^2 \approx 14$ (for the same injected sample amount, linear column velocity and column length). We observed a gain higher than 20 fold, which can be a result of the difference in efficiency and column length between the two columns. Monolithic 20 μm i.d. nanocapillary columns operating at a flow rate 20-50 nL/min may also take an advantage of nanospray ionization to increase MS sensitivity (Emmett et al., 1994). Stable ESI conditions at ultra low flow rate can potentially result in the more efficient transfer of ions into the entrance of the mass spectrometer (Haskins et al., 2001; Shen et al., 2000; Wilm et al., 1994; Valaskovic et al., 1996; Gale et al., 1993; Fenn, 1993 and Kebarle et al., 1993).

Figure 5A:
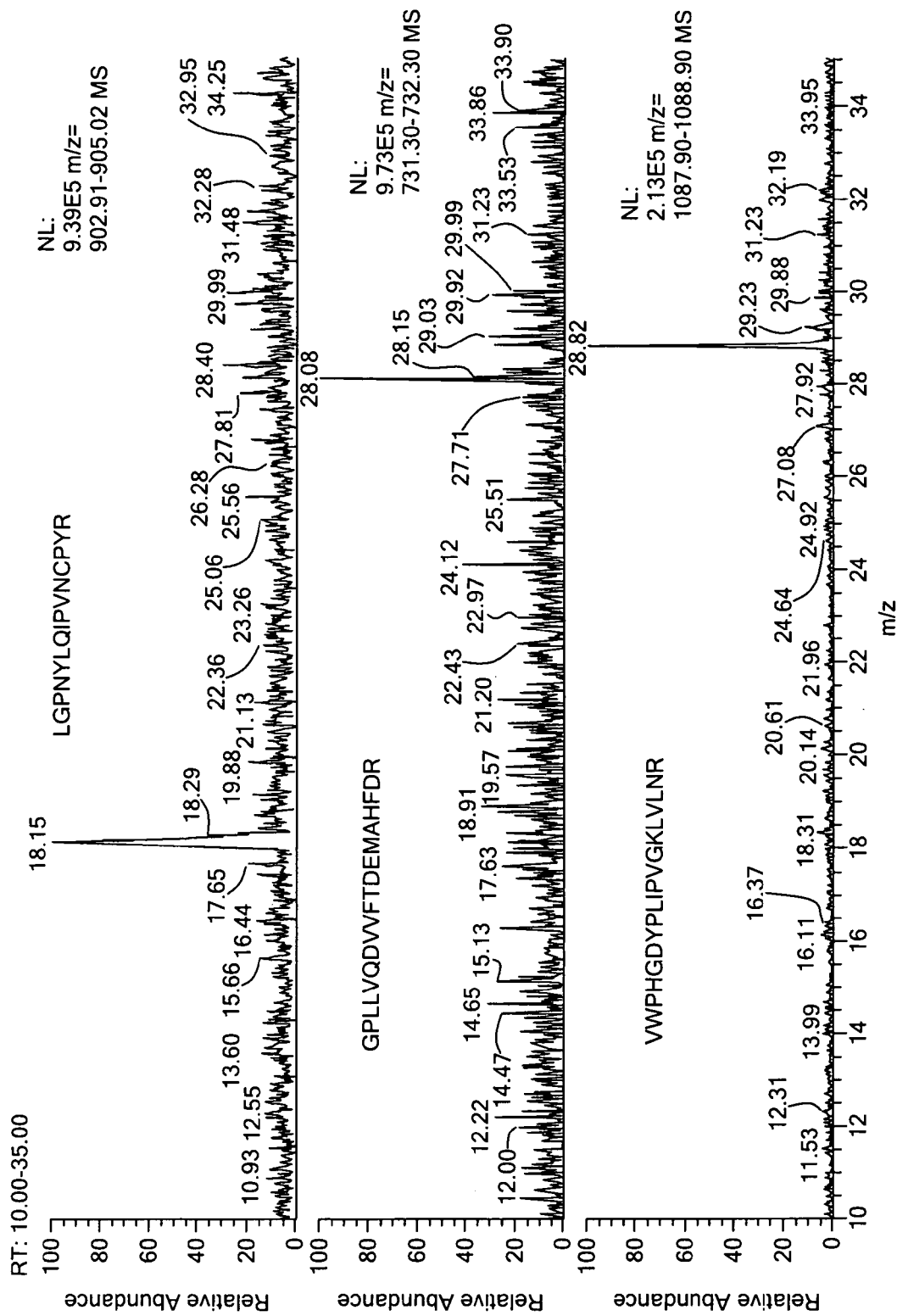
FIGS. 5A and 5B present the results of gradient nano-LC-ESI-MS of 10 amol of a bovine catalase tryptic digest on a monolithic column according to the invention.
Figure 5B:
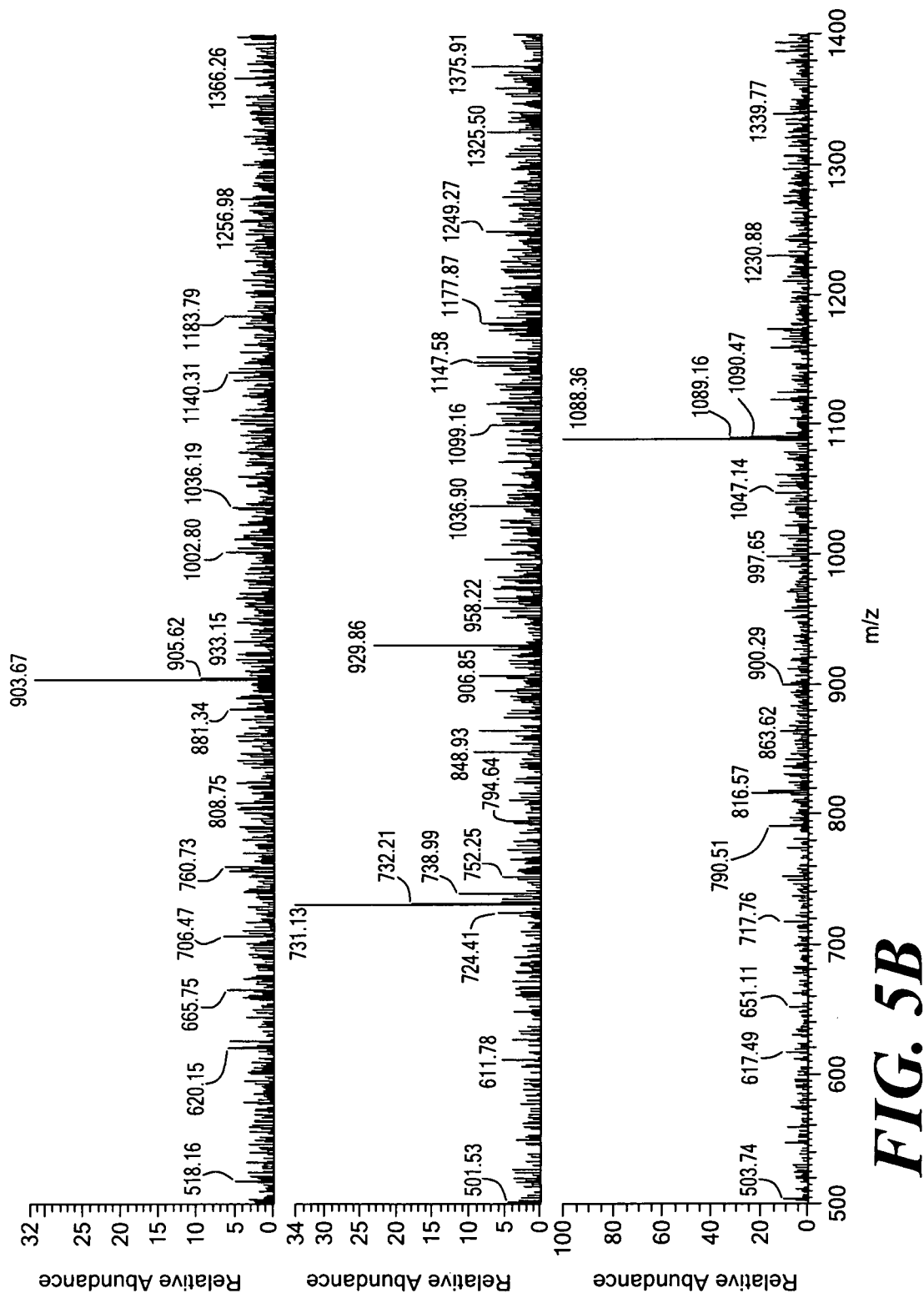
Figure 6A:
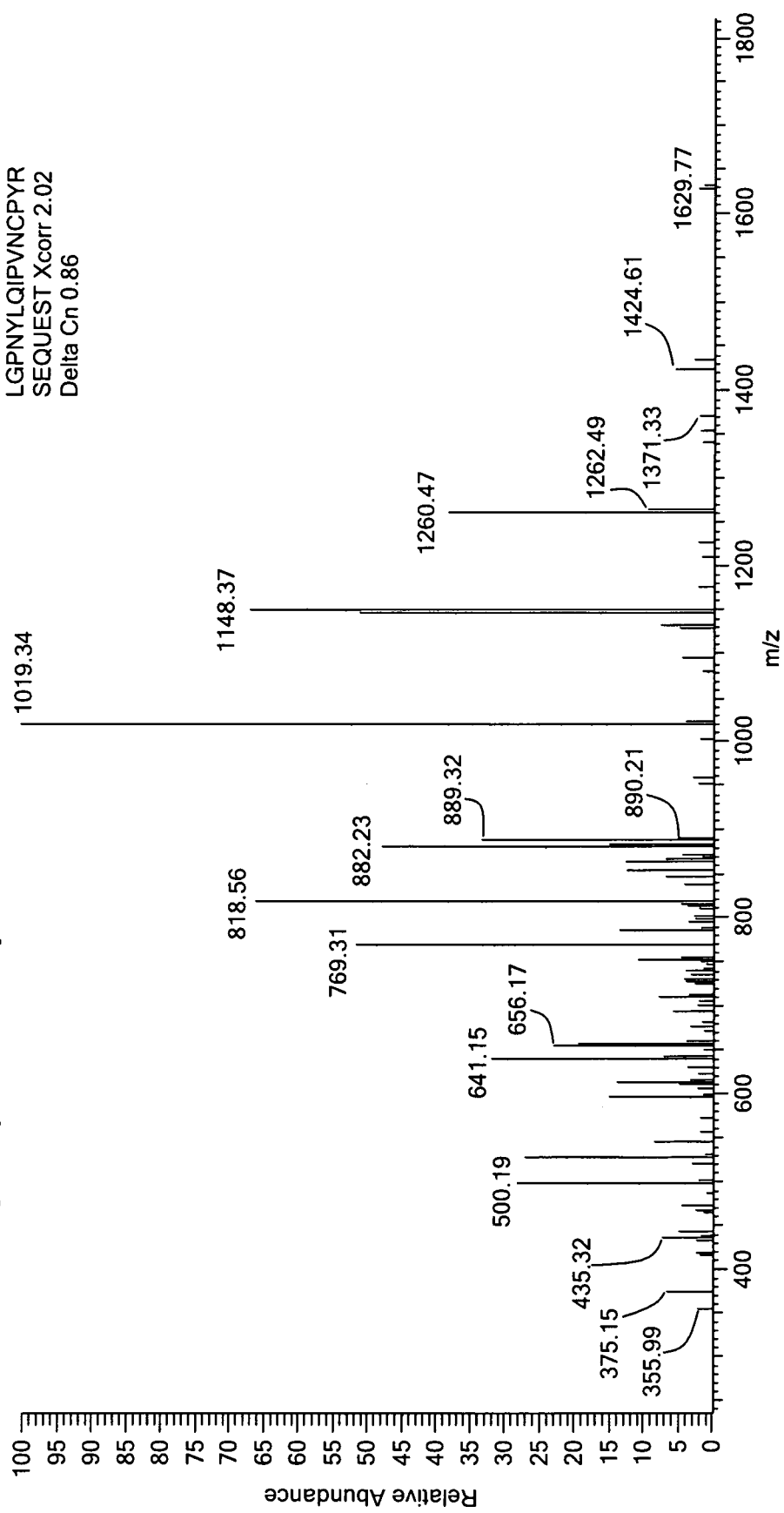
FIG. 6A is an MS/MS spectrum acquired during nano-LC-ESI-MS/MS of the bovine catalase digest shown in FIGS. 5A and 5B.
Figure 6B:
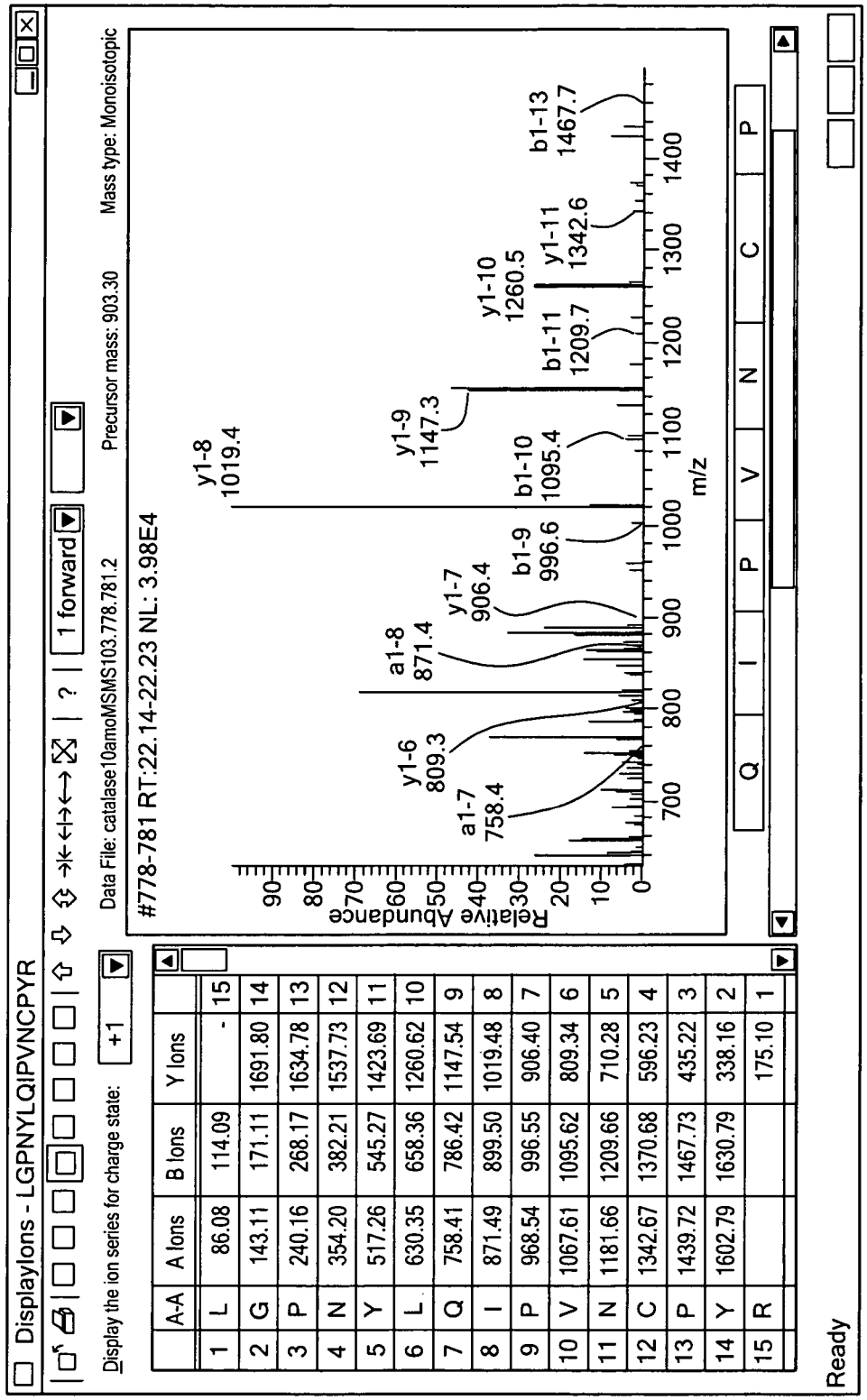
FIG. 6B is a SEQUEST match for the spectrum presented in FIG. 6A.

To illustrate the effectiveness of the nano-LC monolithic columns for the analysis of low abundant analytes, a tryptic digest of bovine catalase was injected at the 10-attomole level on a monolithic nanocapillary column (20 μm i.d.×10 cm). FIG. 5A shows extracted ion chromatograms for selected peptides, and FIG. 5B shows spectra at peak maximum of the same peptides. FIG. 6A is an MS/MS spectrum acquired during nano-LC-ESI-MS/MS of the bovine catalase digest shown in FIGS. 5A and 5B, and FIG. 6B is a SEQUEST match for the spectrum presented in FIG. 6A. Among fourteen peaks corresponding to catalase tryptic peptides observed in the MS mode for the 10 amol of digest injection level, three provided good MS/MS fragmentation and high SEQUEST score.

Figure 7A:
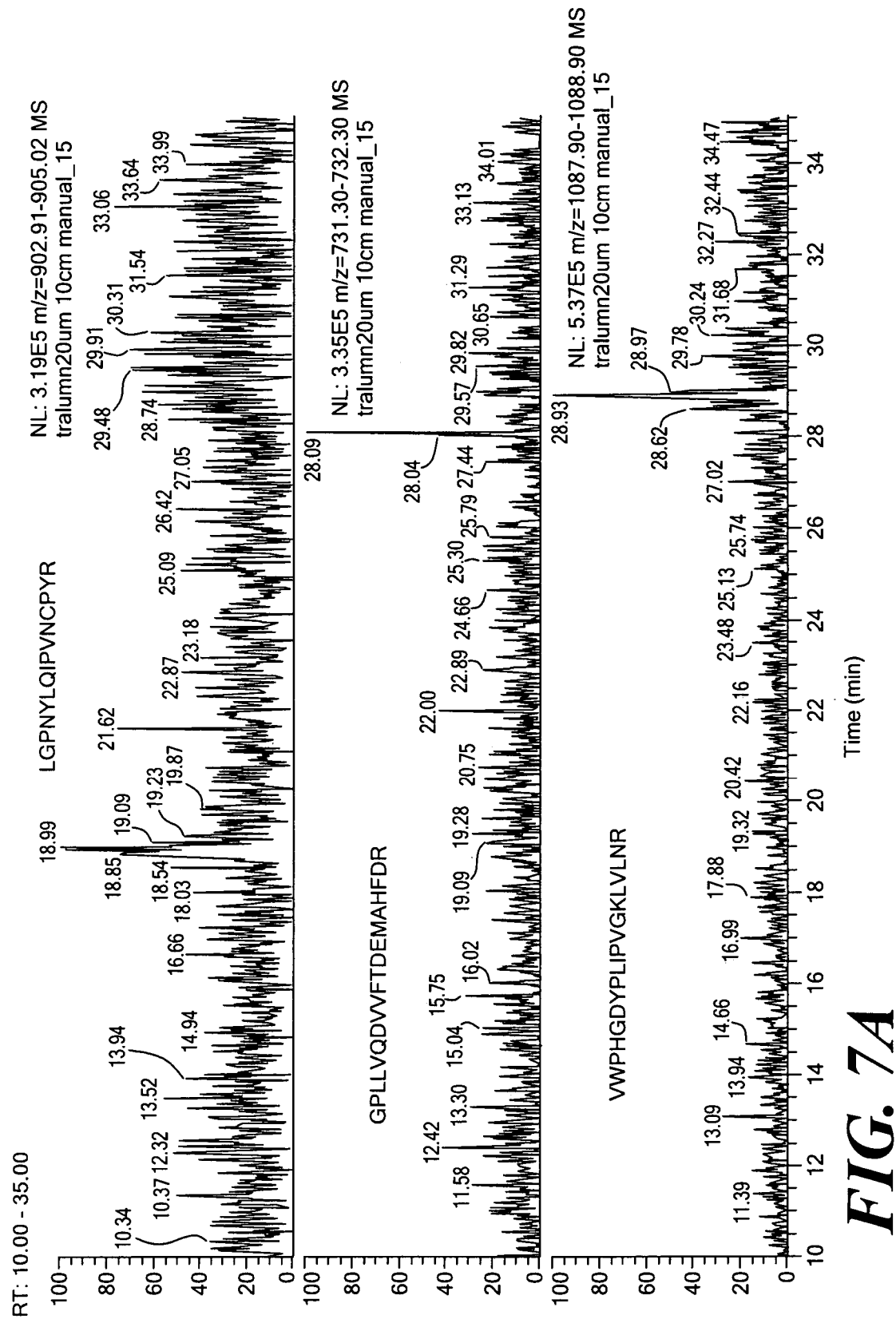
FIGS. 7A and 7B present the results of gradient nano-LC-ESI-MS of 1 amol of a bovine catalase tryptic digest on a monolithic column according to the invention.
Figure 7B:
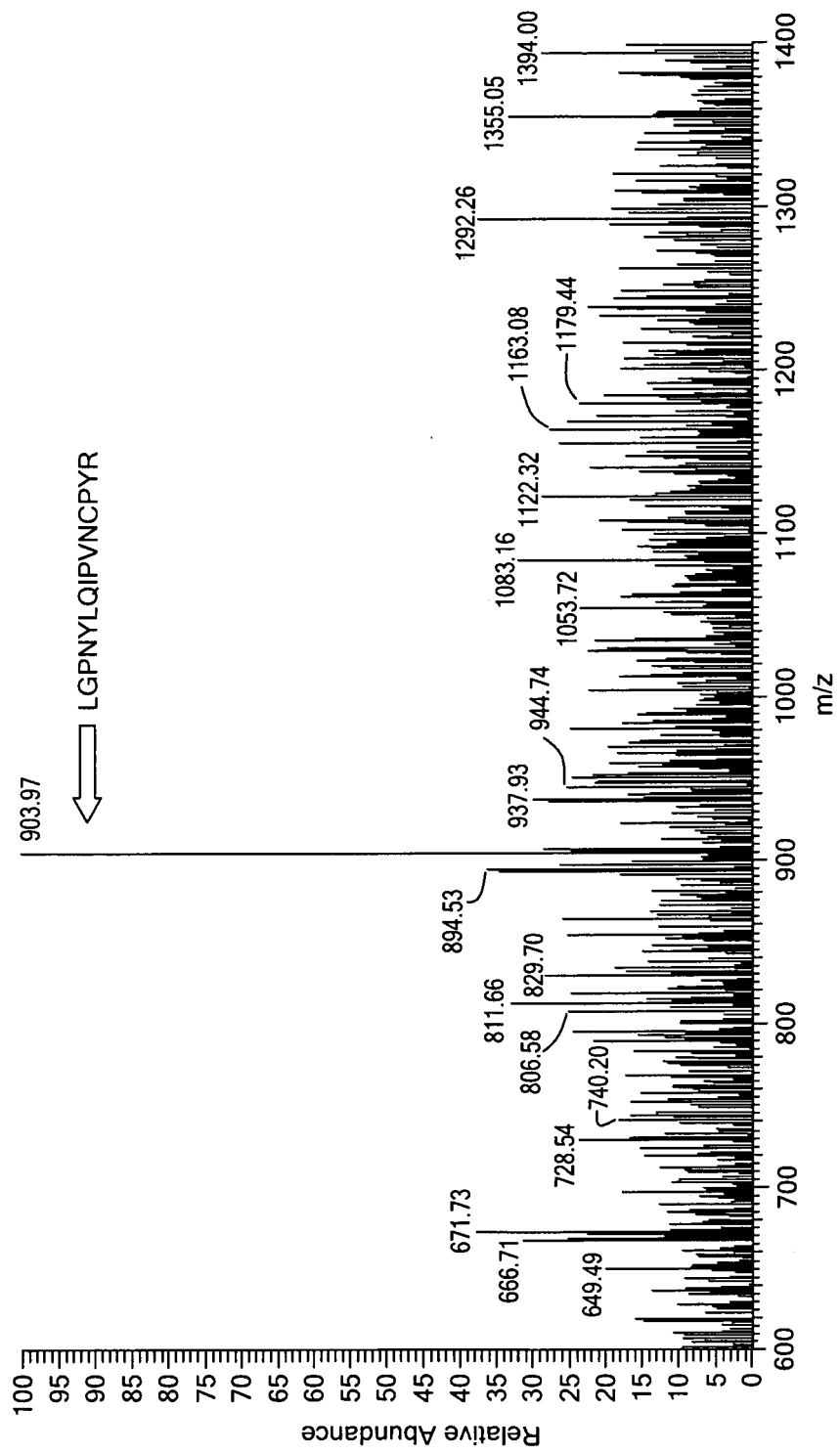
Figure 8A:
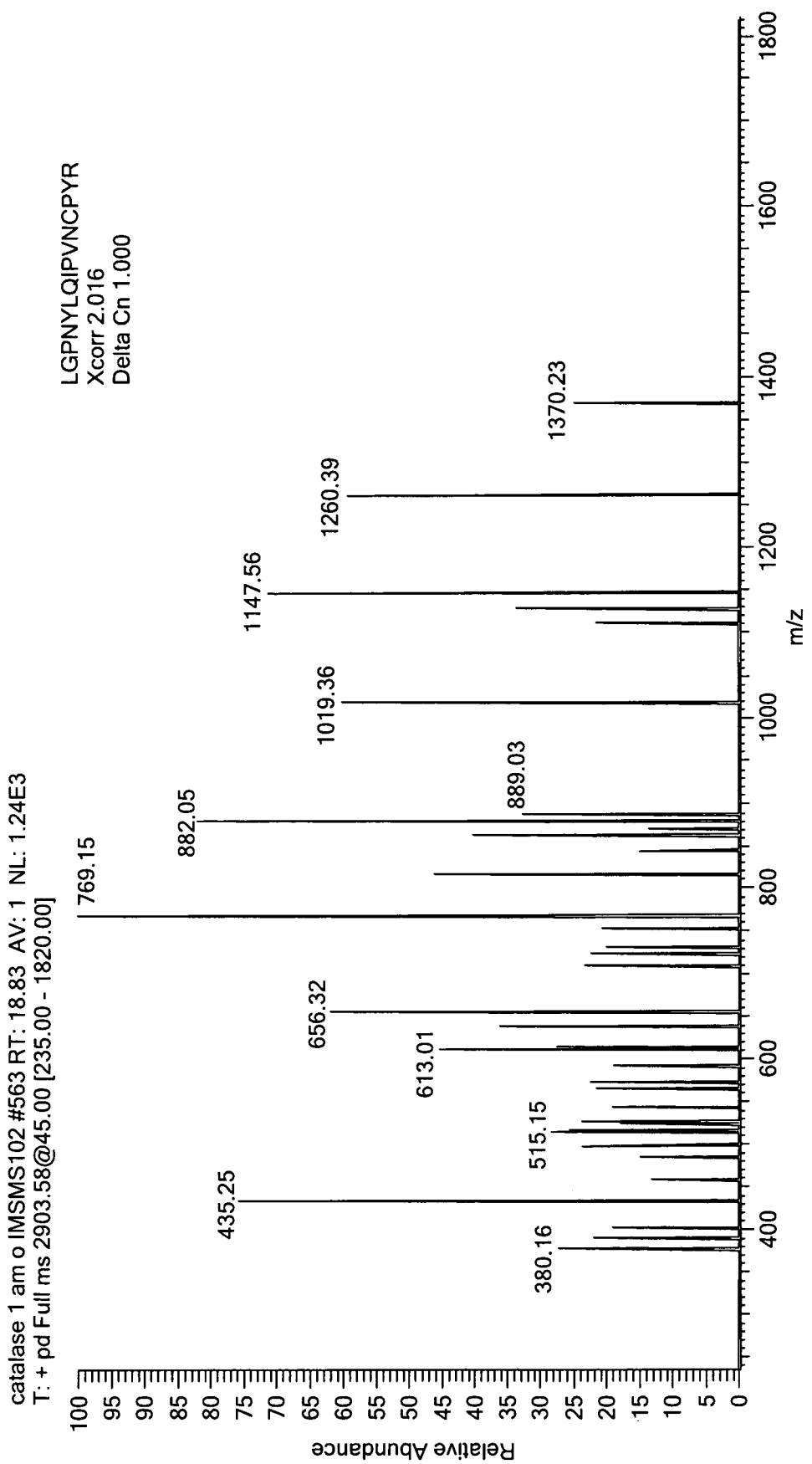
FIG. 8A is an MS/MS spectrum acquired during nano-LC-ESI-MS/MS of the bovine catalase digest shown in FIGS. 7A and 7B.
Figure 8B:
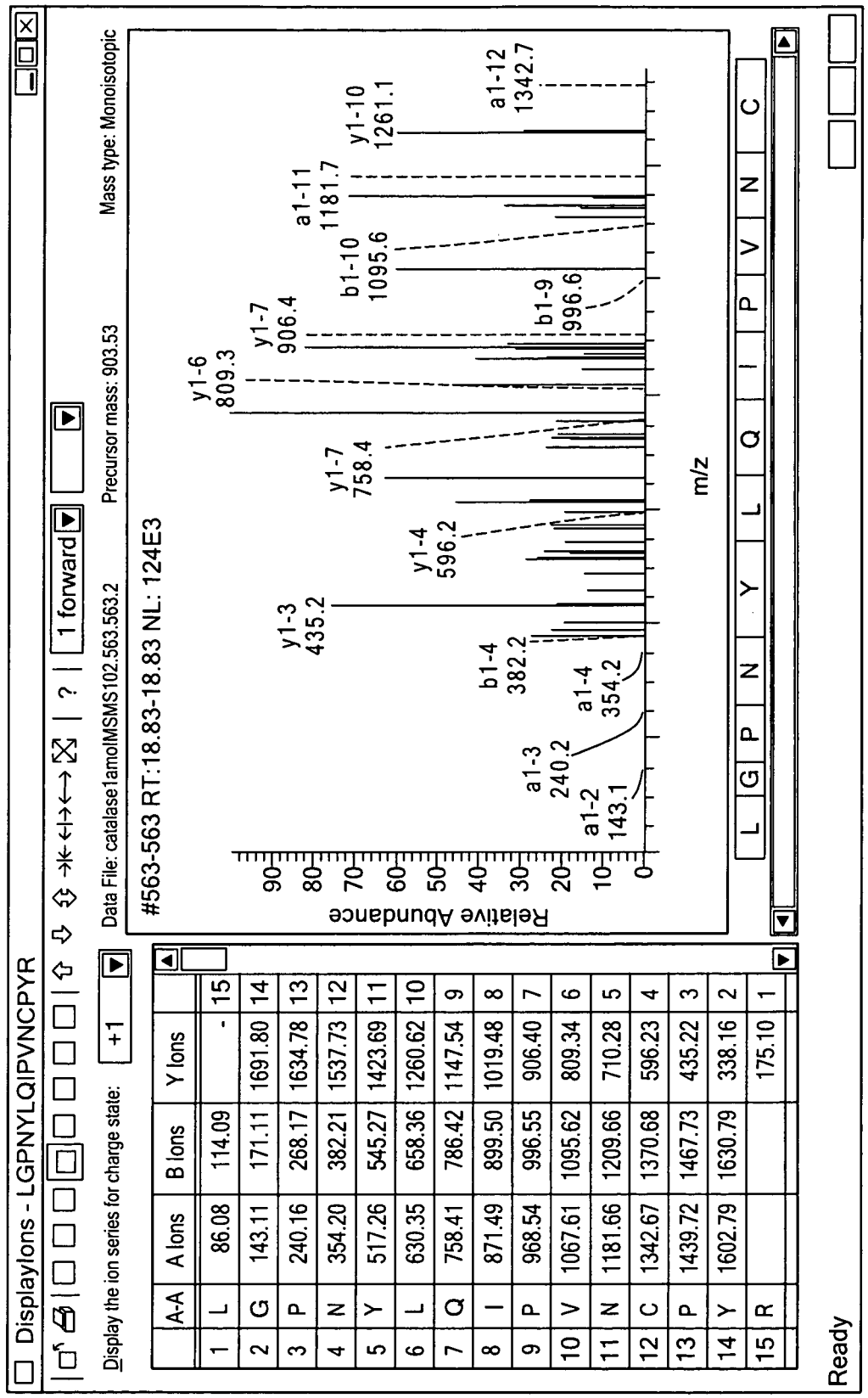
FIG. 8B is a SEQUEST match for the spectrum presented in FIG. 8A.

Next, a tryptic digest of bovine catalase was injected on the column at the 1-attomole level. FIG. 7A presents extracted ion chromatography for this sample level, and FIG. 7B shows a spectrum at peak maximum of the catalase tryptic peptide LGPNYLQIPVNCPYR (SEQ ID NO. 1). Correspondingly, among six peaks observed in the MS mode (S/N≥5) at the 1-amol level, one provided good MS/MS fragmentation and a high SEQUEST score (see FIGS. 8A and 8B). For the specific peptide LGPNYLQIPVNCPYR (SEQ ID NO. 1), reasonable fragmentation patterns, high SEQUEST scores and high reliability of peptide identification (Peng et al., 2003) were obtained at both levels (10 and 1 amol). Typically, a mass sensitivity of 5-10 amol was observed for tryptic peptides in the MS mode at S/N≥5; however, for some peptides, it was almost one order of magnitude higher as expected from the dependence of the ESI-MS signal intensity on the peptide physical properties (Cech et al., 2001 and Cech et al., 2000). A commercial 75 µm i.d.×15 cm packed with 3 µm C18 beads showed mass sensitivity ~200-300 amole for the same bovine catalase tryptic peptides. The number of peptides identified in the MS and MS/MS modes at this level using the 75 µm i.d. column was comparable to that at 5-10 amol level of injection on 20 µm i.d. monolithic column.

Example IV

Figure 9:
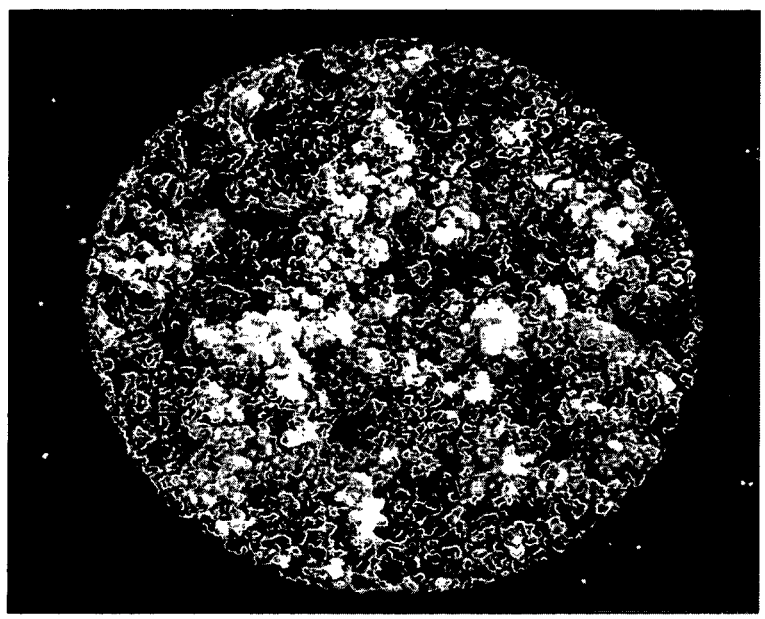
FIG. 9 is a scanning electron micrographs showing cross-sectional views of monolithic packing photopolymerized according to the invention, at 3,500× magnification.
Figure 10A:
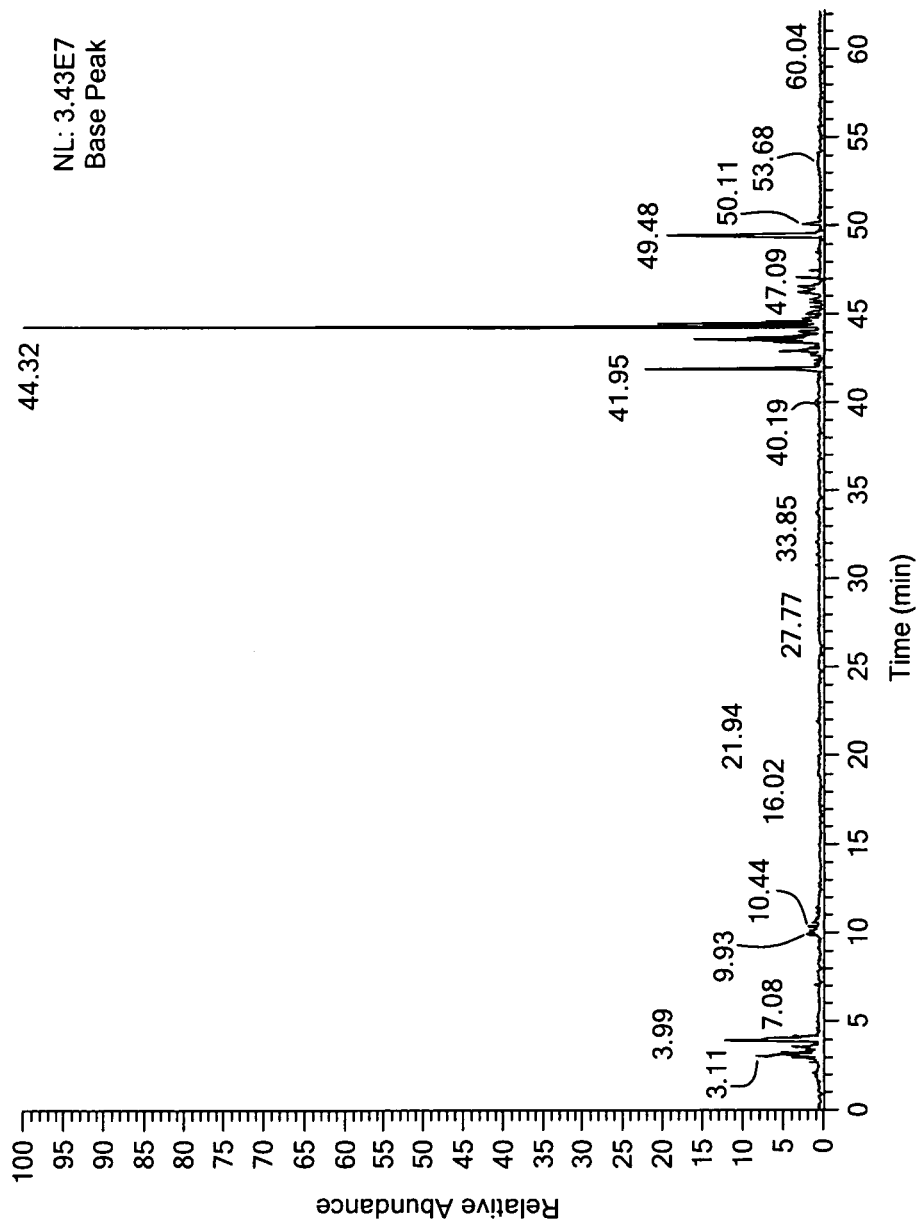
FIG. 10A shows a typical total ion gradient nano-LC/ESI-MS analysis of a tryptic digest of bovine catalase carried out on the column of FIG. 9.
Figure 10B:
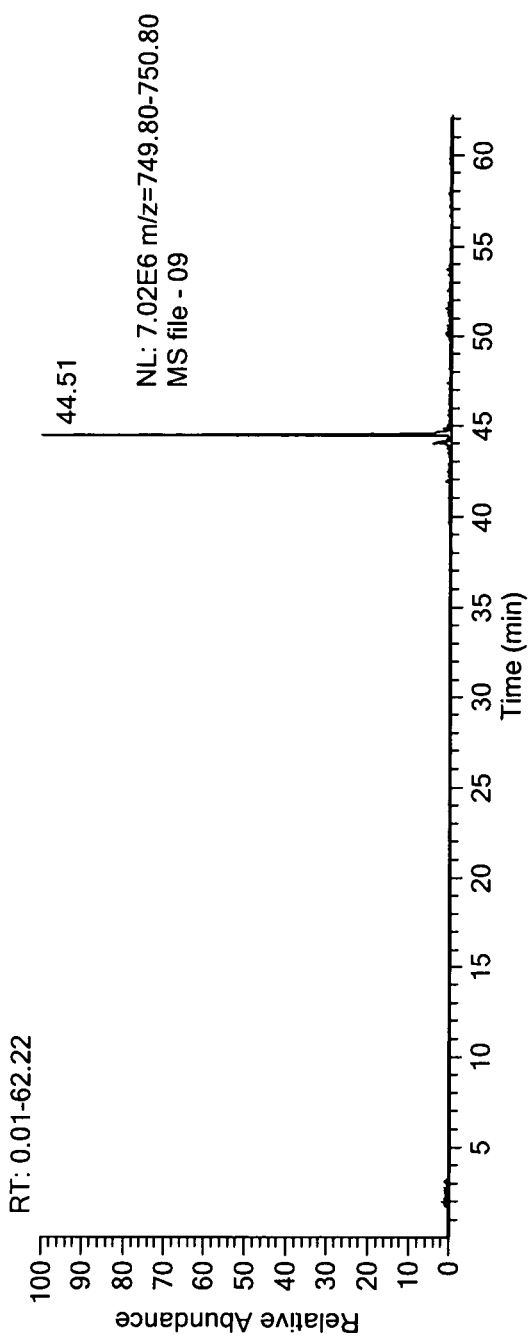
FIGS. 10B-10D show extracted ion chromatograms for selected peptides from the sample separated in FIG. 10A.
Figure 10C:
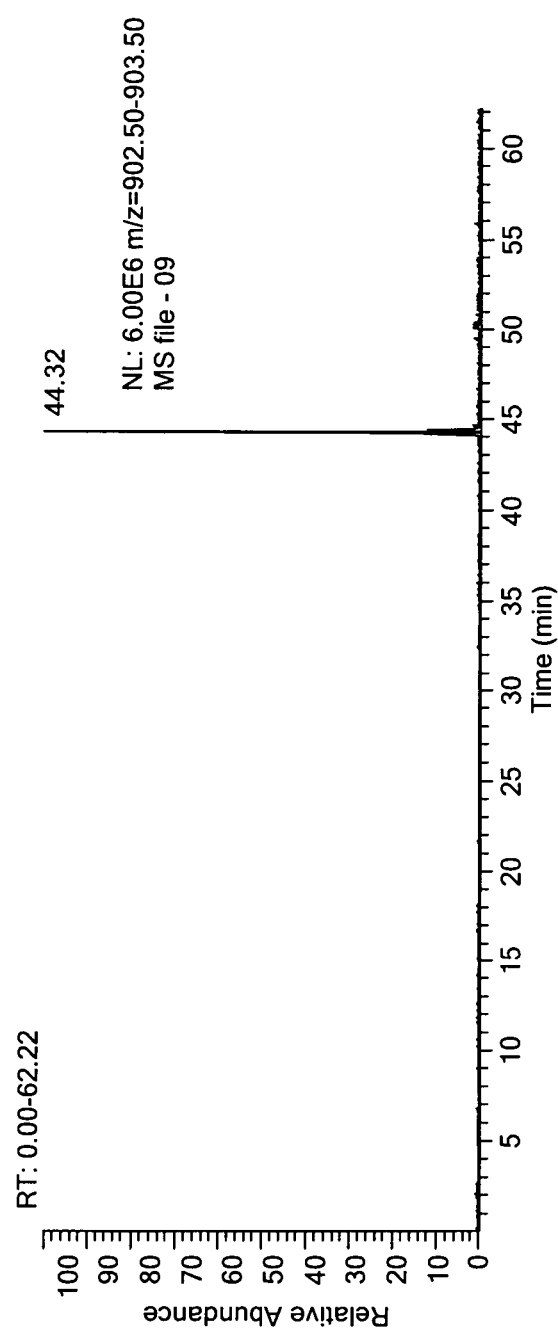
Figure 10D:
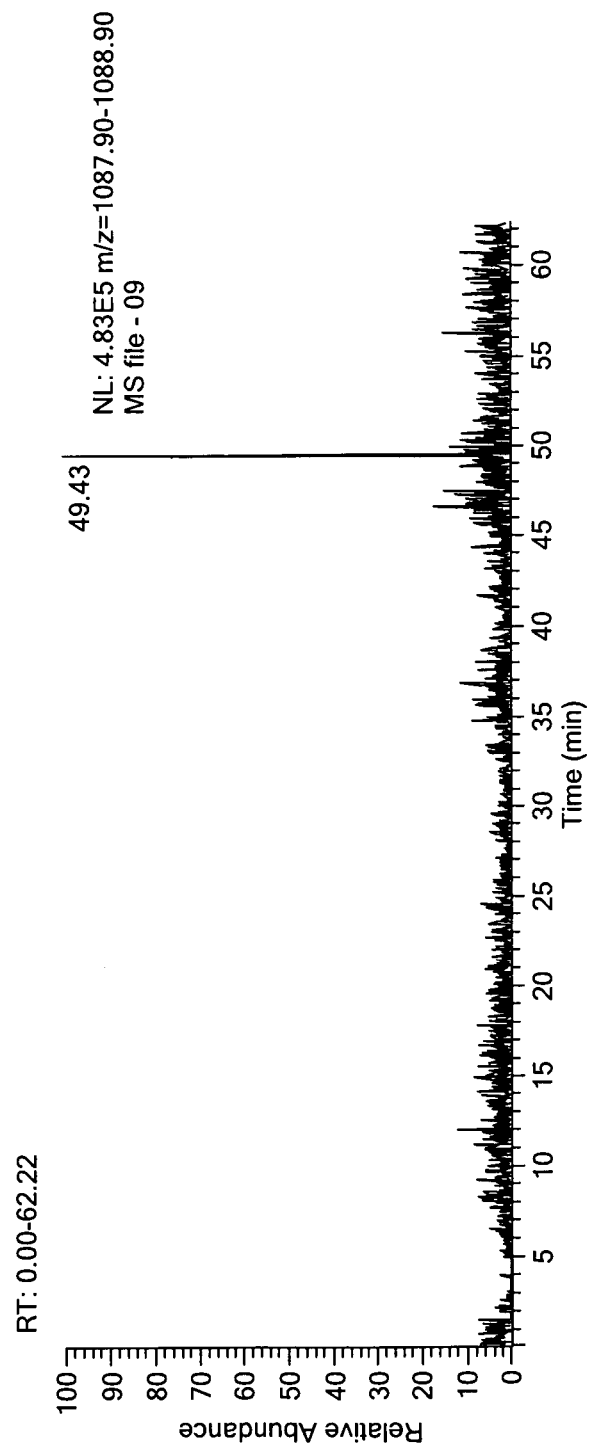

Preparation and Characterization of Low I.D. Methacrylate Monolithic Columns Prepared Using Photopolymerization Column preparation was also carried out using methacrylate monomers and photopolymerization. A typical 1 mL polymerization solution contains monomers of 20% (v/v) stearyl methacrylate (SMA), 20% ethylene glycol dimethacrylate (EGDMA), porogenic solvent of 48% (v/v) 1-propanol, 12% (v/v) methanol and 0.1% (w/v, total monomer) photoinitiator 2,2-dimethoxy-2-phenylacetophenone (DMPAP). The solution was filtered through a cellulose membrane having 0.22-µm pores, and the filtrate was placed into a 1.5 mL glass vial with a LectraBond™ cap and septa from Waters (Milford, Mass.). Afterwards, the filtrate was deaerated with helium to remove dissolved oxygen, and the vial was immediately closed with the cap. A 200 µm i.d. fused-silica capillary connected to a helium source of 50 psi (~344.7 kPa) was inserted into the vial through the cap and the end of the capillary was kept underneath the liquid level to start bubbling. After the bubbling stopped the end of the helium source capillary was pulled above the liquid level. One end of a piece of 0.3 m long 25 µm i.d. silanized capillary was inserted into the vial through the cap and kept underneath the liquid level. With the vial continuously under pressure the polymerization solution quickly filled the silanized capillary tubing and droplets was seen at the other end of the capillary, which was quickly inserted into the vial through the cap and kept below the liquid level. Then the vial with the capillary tubing was placed into the chamber of a Model XL-1500 Spectrolinker™ equipped with 6 UV lamps calibrated at 365 nm (Spectronics Corp., Westbury, N.Y.) and irradiated for 1 h. Thereafter, the capillary was cut off from the vial and flushed extensively with acetonitrile. The capillary column was then blown dry with nitrogen. Column structure was examined with scanning electron microscopy (SEM), and FIG. 9 demonstrates the uniformity of the column structure packed with pseudo-bead particles having a size of 1 µm or less. FIG. 10A shows a typical total ion gradient nano-LC/ESI-MS analysis of a tryptic digest of bovine catalase. Column parameters were: 25 µm i.d.×11 cm; flow rate: ~25 nl/min; sample amount: 10 fmol; mobile phase: A) 100% $H_2O$/0.1% formic acid, B) 100% ACN/0.1% formic acid; gradient: 5%-95% B in 40 min. As can be seen, good separation is obtained, with peaks width of about 15 s. FIGS. 10B-10D are extracted ion chromatograms of the sample of FIG. 10A to show the narrow peak widths obtained in the gradient. This example shows the high performance possible with UV polymerized 25 µm narrow bore columns according to the invention.

Use

Thus, in summary, numerous applications can be envisioned for the ultra-narrow i.d. monolithic capillary columns according to the invention, among which are: high mass sensitivity, high efficiency gradient and isocratic single or multi-dimensional nano-LC analysis of small amounts of biological or clinical samples by coupling to concentration-sensitive detectors (e.g., ESI-MS, UV or fluorescence); single, parallel or sequential sample separation experiments coupled to electrospray ionization mass spectrometry (ESI-MS) or matrix assisted laser desorption ionization (MALDI-) MS; sample desalting prior to MS analysis; sample preconcentration on the head of the column prior to separation, with further analysis; and analysis of complex biological and clinical samples with high dynamic range of components.

The advantages of using monolithic ultra-narrow i.d. capillary columns according to the invention for the separation of biomolecules are numerous. These advantages include; (1) column preparation is simple even for very low i.d. (10-25 µm) ultra low flow nano-LC columns; column preparation does not require expensive equipment such as high-pressure pumps, special adapters, etc.; monolithic ultra-narrow i.d. capillary columns up to 1 meter and longer can be prepared; the small volumes and low amounts of samples available from biochemical, clinical or molecular biological experiments can be analyzed on these columns; retaining frits are not necessary; low backpressure makes the use of very low i.d. (10-25 µm) columns in nano-LC mode possible without special equipment to generate enough bulk flow (pressure bombs, high pressure pumps, etc.); columns with 1 µm pseudo-beads can be made more permeable than packed bed columns having particles of the same size; the enhanced mass transfer properties have a positive effect on separation performance; the low flow rates applied in monolithic columns are ideally suited for on-line coupling with ESI-MS; monolithic columns provide fewer problems with spray tip clogging than particulate columns because of absence of loose particles or particle and frit wreckage; column preparation is inexpensive; temperature induced and UV-light induced polymerization both can be used for column preparation; and even columns with especially narrow i.d. (1-10 µm or less) can be prepared with use of pressurization of the column during the polymerization process and further adjustment of the polymerization mixture composition, if necessarily. Finally, if clogging of the inlet of the column with crude sample occurs, the column can be flushed from the opposite side, or, in the worst case, a short piece (~1 mm) can be cut off from the clogged end and the column can be used without a significant change in performance. In contrast, a particulate capillary column usually has at least one retaining frit at the outlet, and, thus, it cannot be flushed in the direction opposite to the regular elution direction and cannot easily be used after shortening. Therefore, clogging of a particulate capillary column can cause total loss of an expensive separation tool.

APPENDIX b—gradient steepness parameter, $b=\Delta\phi V_0 S/t_g F$;
$t_g$—gradient time;
$\Delta\phi$—difference between the initial and final organic composition in eluent;
$V_0$—column dead volume;
F—flow rate;
$S \approx 0.48 M_w^{0.44} \approx 10$;
k'—capacity factor, $k'=(t_r-t_0)/t_0$;
$t_r$—retention time;
$t_0$—column delay time, $t_0=V_0/F$.

REFERENCES

Adam, T., Unger, K. K., Dittmann, M. M., Rozing, G. P., J. Chromatogr. A. 2000 (a); 887(1-2), 327-37.
Adam, T., Unger, K. K., J. Chromatogr. A. 2000 (b), 894(1-2), 241-51.
Bente, P. F., III, Myerson, J., U.S. Pat. No. 4,810,456, 1989.
Cech, N. B., Enke, C. G., Anal. Chem. 2000, 72(13), 2717-23.
Cech, N. B., Krone, J. R., Enke, C. G., Anal Chem. 2001 Jan. 15; 73(2):208-13.
Emmett, R. M. Caprioli, J. Am. Soc. Mass Spectrom. 1994, 5, 605-613.
Enlund A M, Ericson C, Hjerten S, Westerlund D. Electrophoresis. 2001 Feburary; 22(3):511-7.
Fenn, J. B., J. Am. Soc. Mass Spectrom., 1993, 4, 524-535.
Gale, D. C., R. D., Smith, RCMS 1993, 7, 1017-1021.
Goetzinger, W., Kotler, L., Carrilho, E., Ruiz-Martinez, M. C., Salas-Solano, O., Karger, B. L., Electrophoresis, 1998, 19(2), 242-8.
Gusev, I., Huang, X., Horvath, C., J. Chromatogr A. 1999, 855(1), 273-90.
Haskins, W. E., Wang, Z., Watson, C. J., Rostand, R. R. Witowski, S. R., Powell, D. H., Kennedy, R. T., Anal. Chem., 2001, 73(21), 5005-5014.
Huang, X., Zhang, S., Schultz, G. A., Henion, J. Anal. Chem. 2002, 74(10), 2336-44.
Huber. C., Oberacher, H., Premstaller, A., U.S. patent application No. #0088753 A1, 2002.
Ishizuka, N., Minakuchi, H., Nakanishi, K., Soga, N., Nagayama, H., Hosoya, K., Tanaka, N. Anal. Chem. 2000 Mar. 15, 72(6), 1275-80.
Kebarle, P., Tang, L., Anal. Chem., 1993, 65, 972A-986A.
Licklider, L. J., Thoreen, C. C., Peng, J., Gygi, S. P., Anal Chem. 2002; 74(13), 3076-83.
MacNair, J. E., Patel, K. D., Jorgenson, J. W., Anal. Chem. 1999 Feb. 1; 71(3):700-708.
Meyers, J. J., Liapis, A. I., J. Chromatogr. A, 1999, 852, 3-23.
Moore, R. E., Licklider, L., Schumann, D., Lee, T. D., Anal. Chem. 1998, 70(23), 4879-84.
Novotny, M. V., Ishii, D., J. Chromatogr. Lib., 1985, 30, Chapters 1-3.
Peng, J., Elias, J. E., Thoreen, C. C., Licklider, L. J., Gygi, S. P., J. Proteome Research., 2003, 2, 43-50.
Peters, E. C., Petro, M., Svec, F., Fréchet, J. M., Anal. Chem. 1998, 70(11), 2296-302.
Petro, M., Svec, F., Frechet, J. M. J., J. Chromatogr. A, 1996, 752, 59-66.
Premstaller, A., Oberacher, H., Huber, C. G. Anal. Chem. 2000, 72(18), 4386-93.
Premstaller, A., Oberacher, H., Walcher, W., Timperio, A. M., Zolla, L., Chervet, J. P., Cavusoglu, N., van Dorsselaer, A., Huber, C. G. Anal. Chem. 2001, 73(11), 2390-6.
Rohr, T., E. F. Hilder, J. J. Donovan, F. Svec, J. M. J. Fréchet, Macromolecules 2003, 36, 1677-1684.
Seidl, J., Heitz, W., Adv. Polym. Sci., 1967, 5, 113-213.
Shen, Y., Zhao, R., Berger, S. J., Anderson, G. A., Rodriguez, N., Smith, R. D., Anal. Chem. 2002 Aug. 15; 74(16):4235-49.
Snyder, L. R., Stadalius, M. A., Quarry, M. A., Anal. Chem., 1988, 55, 1412 A-30A.
Stadalius, M. A., Gold, H. S., Snyder, L. R., J. Chromatogr., 296, 1884, 31.
Svec, F., Frechet, J. M. J., Macromolecules 1995, 28, 7580-7582.
Tennikov, M. B., Gazdina N. V., Tennikova, T. B., Svec, F., J. Chromatogr. A, 1998, 798(1-2), 55-64.
Unger, K. K., Packings and Stationary Phases in Chromatographic Techniques, Unger, K. K., Ed.; Marcel Dekker: New York, 1990.
Valaskovic, G. A., Kelleher, N. L., McLafferty, F. W., Science. 1996; 273, 1199-202.
Wilm, M., Mann M., Int. J. Mass Spectrom. Ion Proc. 1994, 136, 167-180.
Wu, N., Lippert, J. A., Lee, M. L., J. Chromatogr A. 2001, 911(1):1-12. Wu, S. L., Hancock, W. S., Goodrich, G. G., Kunitake, S. T., Proteomics, 2003, In Press.
Xie, S., Allington, R. W., Svec, F., Fréchet, J. M., J. Chromatogr. A. 1999, 865(1-2), 169-74.
Zhang, S., Huang, X., Zhang, J., Horváth, C., J. Chromatogr A. 2000, 887(1-2), 465-477.

While the present invention has been described in conjunction with a preferred embodiment, one of ordinary skill, after reading the foregoing specification, will be able to effect various changes, substitutions of equivalents, and other alterations to the compositions and methods set forth herein. It is therefore intended that the protection granted by Letters Patent hereon be limited only by the definitions contained in the appended claims and equivalents thereof.

What is claimed is:

1. A batch of separation capillary columns or channels in one or more microfabricated devices, each of said columns or channels comprising:
   a monolithic separation medium comprising a macroporous, rigid, continuous polymeric structure, wherein said polymeric structure is attached covalently to the wall of said column or channel, wherein said column or channel has an i.d. of 25 μm or less, wherein the efficiency of operation of said column or channel is greater than 100,000 theoretical plates per meter; and
   wherein the column-to-column reproducibility of retention time within the batch during use varies less than 10%.

2. The capillary column or channel of claim 1, wherein the reproducibility of retention time during use varies less than 5%.

3. The capillary column or channel of claim 1, wherein said column or channel has an i.d. of 10 μm or less.

4. The capillary column or channel of claim 1, wherein the efficiency of operation of said column or channel is greater than 200,000 theoretical plates per meter.

* * * * *